(12) United States Patent
Kube et al.

(10) Patent No.: US 11,103,166 B2
(45) Date of Patent: Aug. 31, 2021

(54) SENSOR SYSTEM AND METHOD FOR MANUFACTURING THEREOF

(71) Applicant: Roche Diabetes Care, Inc., Indianapolis, IN (US)

(72) Inventors: Oliver Kube, Mannheim (DE); Helmut Walter, Heppenheim (DE); Alexander Poggenwisch, Colgenstein (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 110 days.

(21) Appl. No.: 16/615,702

(22) PCT Filed: May 22, 2018

(86) PCT No.: PCT/EP2018/063321
§ 371 (c)(1),
(2) Date: Nov. 21, 2019

(87) PCT Pub. No.: WO2018/215421
PCT Pub. Date: Nov. 29, 2018

(65) Prior Publication Data
US 2020/0221984 A1 Jul. 16, 2020

(30) Foreign Application Priority Data
May 23, 2017 (EP) .................................... 17172533

(51) Int. Cl.
*A61B 5/145* (2006.01)
*A61B 5/00* (2006.01)

(52) U.S. Cl.
CPC ........ *A61B 5/14546* (2013.01); *A61B 5/0015* (2013.01); *A61B 5/6833* (2013.01); *A61B 5/6848* (2013.01); *A61B 2562/12* (2013.01)

(58) Field of Classification Search
CPC .. A61B 5/145; A61B 5/14532; A61B 5/14546
See application file for complete search history.

(56) References Cited

U.S. PATENT DOCUMENTS

2008/0114280 A1 5/2008 Stafford
2011/0077490 A1 3/2011 Simpson et al.
(Continued)

FOREIGN PATENT DOCUMENTS

JP 2012531946 12/2012
WO WO 2007/064130 7/2007
(Continued)

*Primary Examiner* — Eric F Winakur
*Assistant Examiner* — Alice Ling Zou
(74) *Attorney, Agent, or Firm* — Woodard, Emhardt, Henry, Reeves & Wagner, LLP

(57) ABSTRACT

A sensor system (110), a method of manufacturing a flexible electronics patch (114) for use in a sensor system (110) and a method of manufacturing a sensor system (110). The sensor system (110) comprises—at least one analyte sensor (112) configured for at least partial implementation into a body tissue of a user; —at least one flexible electronics patch (114), the flexible electronics patch (114) comprising—at least one applicator unit (134) for applying the flexible electronics patch (114) to the skin (132) of the user; and —at least one second adhesive layer (136) for adhering the flexible electronics patch (114) to the applicator unit (134) before applying the flexible electronics patch (114) to the skin (132) of the user.

13 Claims, 12 Drawing Sheets

(56) References Cited

U.S. PATENT DOCUMENTS

Figure 1:
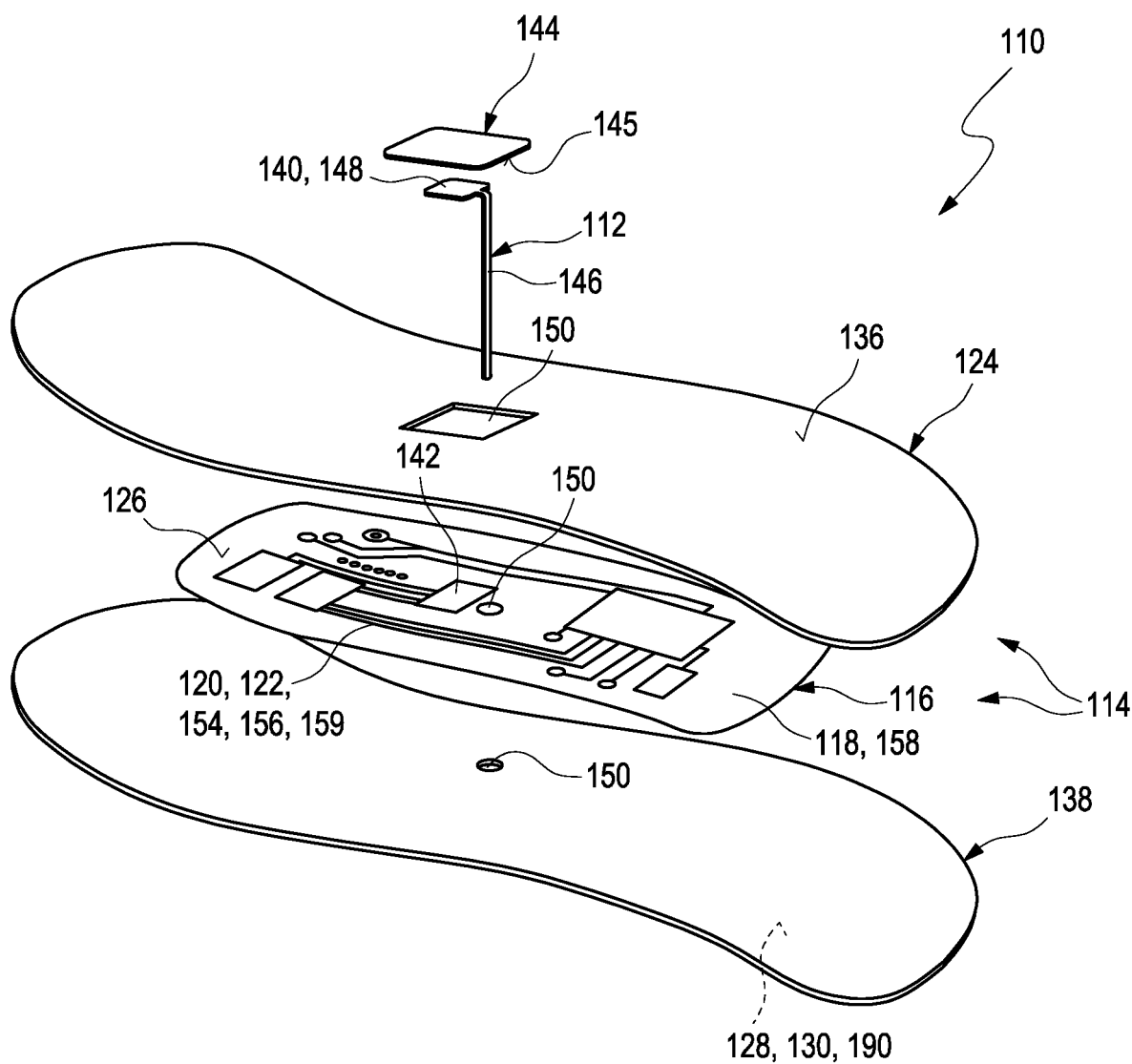

2015/0005589 A1    1/2015  Bly et al.
2017/0027514 A1 *  2/2017  Biederman .......... A61B 5/1451

FOREIGN PATENT DOCUMENTS

| WO | WO 2013/066854    |        | 5/2013  |                |
|----|-------------------|--------|---------|----------------|
| WO | WO-2014018928 A1  | *      | 1/2014  | ............. A61B 5/153 |
| WO | WO-2017070360 A1  | *      | 4/2017  | ........... A61B 5/6833 |

* cited by examiner

SENSOR SYSTEM AND METHOD FOR MANUFACTURING THEREOF

FIELD OF THE INVENTION

The invention relates to a sensor system and to a method of manufacturing a flexible electronics patch for use in a sensor system as well as to a method of manufacturing the sensor system. The devices and methods according to the present invention may mainly be used for long-term monitoring of an analyte concertation in a body fluid, such as for long-term monitoring of a blood glucose level or of the concentration of one or more other types of analytes in a body fluid. The sensor system specifically may comprise at least one transcutaneous analyte sensor and/or at least one subcutaneous analyte sensor. The invention may both be applied in the field of home care as well as in the field of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring, specifically by using one or both of a transcutaneous analyte sensor or a subcutaneous analyte sensor, such as an implanted sensor chip. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as photo resist layers or the like.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown e.g. in DE 954712 B. Other techniques of providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical parts and contacts by using appropriate seals is known from e.g. DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

WO 2011/041463 A2 discloses a transcutaneous sensor device configured for continuously measuring analyte concentrations in a host. In some embodiments, the transcutaneous sensor device comprises an in vivo portion configured for insertion under the skin of the host and an ex vivo portion configured to remain above the surface of the skin of the host after sensor insertion of the in vivo portion. The in vivo portion may comprise a tissue piercing element configured for piercing the skin of the host and a sensor body comprising a material or support member that provides sufficient column strength to allow the sensor body to be pushable in a host tissue without substantial buckling. The ex vivo portion may be configured to comprise (or operably connect to) a sensor electronics unit and may comprise a mounting unit. Also described here are various configurations of the sensor body and the tissue piercing element that may be used to protect the membrane of the sensor body.

US 2012/0253145 A1 discloses systems and methods for transcutaneously implanting medical devices, such as in vivo analyte sensors. The systems and methods involve the use of introducers or inserters made of shape memory alloy (SMA) materials which are transitionable from one operative state or configuration to another operative state or configuration, wherein the transition from state to state enables the transcutaneous implantation and/or transcutaneous explantation of the medical device.

Despite the advantages and the progress achieved by the above-mentioned developments, specifically in the field of continuous monitoring technology, some significant technical challenges remain. An assembly of a plurality of components is generally required, which typically implies a complex and costly manufacturing process. Further, known techniques generally require voluminous components, which is an issue, specifically considering the fact that miniaturizing the sensor systems is a factor contributing to the convenience of use. Further, many sensor systems typically comprise the use of voluminous and rigid electronics for sensor controller, typically worn on the upper arm or belly of the user. The voluminous electronics patch, typically, is mounted to the skin by a plaster. These setups, however, typically have a tendency to detach from the skin, since the electronics components often are unable to follow the movements of the soft skin and tissue of the human body. A further challenge arises from the fact that moisture and vapor may arise from the skin. Typical electronics components are not sufficiently breathable and, further, detrimental effects for the electronics components and electrical leads may arise from the moisture, and the moisture may further lead to a detaching of the electronics components from the skin.

Problem to be Solved

It is therefore an objective of the present invention to provide a sensor system which fully or partially avoids the above-mentioned technical problems and addresses the technical challenges of skin-worn sensor electronics. Specifically, a sensor system having an electronics patch shall be disclosed which increases the comfort of the user, which at least partially avoids the problem of detaching from the skin and which, still, may easily be applied to the skin.

SUMMARY OF THE INVENTION

This problem is solved by a sensor system and methods with the features of the independent claims. Preferred embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such a way with other optional or non-optional features of the invention.

In a first aspect of the present invention, a sensor system is disclosed. As used herein, the term "sensor" may generally refer to an arbitrary element which is capable of detecting at least one measurable property, such as a chemical property like e.g. the presence or absence of at least one predetermined substance, a concentration of at least one predetermined substance, a physical property such as a pressure and/or a temperature, or a biological property. As further used herein, a "system" generally may refer to a combination of two or more interacting components which interact in such a way that at least one common function is performed by the system. The components of the system generally may be combined into a unitary device or may mechanically be separated. Consequently, a "sensor system" may generally refer to a system functioning as a sensor or contributing to the functionality of a sensor.

The sensor system comprises at least one analyte sensor configured for at least partial implementation into a body tissue of a user. As used therein, the term "analyte sensor" may generally refer to an arbitrary element which is adapted to perform a process of detection and/or which is adapted to be used in the process of detection of at least one analyte. Thus, the sensor specifically may be adapted to determine the concentration of the analyte and/or a presence of the analyte. The term "analyte" may generally refer to at least one predetermined substance or compound to be detected, such as at least one chemical substance, e.g. at least one metabolite and/or at least one substance present in the human body. As an example, without limiting further applications, the analyte may be or may comprise glucose. The term "detection" may generally refer to a process of determining a presence and/or a quantity and/or a concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

In order to be configured for at least partial implantation into the body tissue of the user, the analyte sensor may fulfill certain properties rendering the analyte sensor suitable for the named purpose. Thus, as an example, the analyte sensor may have a dimension which allows for implementation. As an example, the analyte sensor, in at least one dimension, may have an extension not exceeding 50 mm, preferably not exceeding 40 mm. As an example and as will be outlined in further detail below, the analyte sensor specifically may be flexible, in order to follow the movement of the human body. As an example, the analyte sensor may be or may comprise a flexible sensor strip, having an extension of no more than 30 mm in a longitudinal direction and a width of no more than 3 mm in a direction perpendicular to the longitudinal direction. Further, in order to be suited for full or partial implementation, the analyte sensor may have a coating which renders the analyte sensor biocompatible, such as a membrane coating. As further used herein, the term "for at least partial implantation into the body tissue" generally may refer to the possibility that the analyte sensor is fully implanted into the body tissue, without any part of the analyte sensor protruding through the skin of the user, i.e. a full subcutaneous implantation. Alternatively, a part of the analyte sensor may protrude through the skin of the user, such that a portion, e.g. a contacting portion, is located outside the body tissue, and another portion, e.g. a measurement portion having one or more electrodes thereon, is located inside the body tissue, i.e. a transcutaneous implementation.

The sensor system further comprises at least one flexible electronics patch. As used herein, the term "patch" may generally refer to a flat article, having a lateral dimension exceeding its thickness, e.g. by at least a factor of two or at least a factor of three or five. As an example, the patch may have a round, oval, circular, rectangular or polygonal shape in a plane of lateral extension, such as the shape of a plaster. As further used herein, the term "electronics patch" may generally refer to a patch having at least one electronic function. As an example, the electronics patch generally may have at least one functionality selected from the group consisting of: a functionality of reading measurement data from the analyte sensor, a functionality of controlling the analyte sensor, a functionality of collecting measurement data and storing measurement data, a functionality of transmitting analyte data, e.g. to at least one data reader external from the electronics patch, e.g. by wireless data transmission. The electronics patch, as an example, may have at least one of a voltage measurement device, a current measurement device, an electrical current source, an electrical voltage source. As further used herein, the term "flexible" generally refers to the property of being one or both of bendable, shapeable or stretchable, e.g. by forces typically occurring within the human body. Thus, as an example, the flexible electronics patch, at least in part, specifically the flexible substrate which will be discussed in further detail below, may at least have the flexibility of a sheet of typical typewriting or printing paper. Ideally, the flexible electronics patch, at least in part and specifically referring to its flexible substrate, may at least have the flexibility of human skin or even better.

The flexible electronics patch comprises
- at least one flexible circuit board having a flexible substrate and a plurality of conductive paths on the flexible substrate;
- at least one electronics component for performing at least one analyte measurement using the analyte sensor, the electronics component being one or both of attached to or integrated into the flexible circuit board;
- at least one flexible protective layer, the protective layer at least partially covering an upper side of the flexible circuit board; and
- at least one first adhesive layer on a lower side of the flexible electronics patch, configured for adhering the flexible electronics patch to the skin of the user.

As used therein, the term "circuit board" generally may refer to an arbitrary element capable of carrying at least one conductive path thereon, such as at least one conductive lead. As an example, the circuit board may be a flat circuit board, having a lateral extension exceeding its thickness by far, such as by at least a factor of 10, more preferably at least a factor of 50 or even a factor of 100 or more. In a top view onto a plane of extension, the circuit board, as an example, may have a round, a circular, an oval, a rectangular or a polygonal shape. Other shapes generally are feasible. As further used herein, the term "flexible circuit board" generally may refer to a circuit board being flexible in the sense defined above. Consequently, the term "substrate" generally may refer to a carrier being capable of carrying one or more additional components, such as the one or more conductive paths and, additionally and optionally, one or more electronics components. The substrate, as will be outlined in further detail below, specifically may be or may comprise at least one foil, such as at least one plastic foil. Consequently, the term "flexible substrate" generally refers to a substrate being flexible in the sense defined above.

As further used herein, the term "conductive path" may generally refer to an electrically conductive element creating an electrical connection between at least two points or regions on the substrate. Thus, as an example, the electrically conductive path generally may be or may comprise one or more straight, curved, bent or angled lines, e.g. printed lines of at least one conductive material on the substrate. Additionally or alternatively, the at least one conductive path may also comprise at least one contact pad.

As further used herein, the term "electronics component" may generally refer to an element or device capable of performing at least one electronic function. The electronics component, as an example, may be or may comprise at least one of an active electronics component or a passive electronics component. Specifically, the at least one electronics component may comprise at least one of a voltage measurement device, a current measurement device, a current source or a voltage source, for performing the analyte measurement using the light sensor. As an example, the at least one electronics component may be or may comprise at least one integrated circuit, specifically at least one application-specific integrated circuit (ASIC). The integrated circuit, specifically the at least one application specific integrated circuit, may comprise the functionality for performing the at least one analyte measurement by using the analyte sensor, e.g. by providing one or more of an appropriate potentiometric, potentiostatic or amperometric measurement device, which, in conjunction with at least one working electrode of the analyte sensor and at least one further electrode, e.g. a counter electrode and/or a reference electrode of the analyte sensor, may perform at least one electrochemical analyte measurement. Additionally or alternatively, however, the at least one electronics component may also comprise at least one contactless readout device for reading out measurement data of a subcutaneous analyte sensor.

As outlined above, the at least one electronics component is one or both of attached to or integrated into the flexible circuit board. As an example, the at least one electronics component may be soldered to one or more appropriate contact pads on the flexible circuit board. Additionally or alternatively, the at least one electronics component may be electrically connected to one or more appropriate contact pads on the flexible circuit board by at least one electrically conductive adhesive. Further, additionally or alternatively, the at least one electronics component may be integrated into the flexible circuit board, e.g. by printing an appropriate resistive structure onto the flexible circuit board, e.g. a resistive bridge or the like. Further, additionally or alternatively, electronics may be printed onto the flexible circuit board e.g. by using printable conductive or semiconducting inks, such as polymer inks, e.g. by printing one or more transistors. Various possibilities may be realized.

As further used herein, the term "protective layer" generally refers to a combination of one or more layers of material which fully or partially cover an upper side of the flexible circuit board, specifically the at least one electronics component attached thereto or integrated therein and/or at least one conductive path on the flexible substrate. The at least one protective layer generally may protect, at least partially, the at least one flexible circuit board from one or more of: moisture, environmental effects or mechanical shocks. Thus, as an example, the at least one protective layer may prevent the one or more electronics components from detaching from the flexible circuit board and/or may protect the one or more electronics components and/or the one or more conductive paths from mechanical damages such as scratches or the like. Further, the influence of moisture on the reliability of the electronics patch may be reduced, such that the electronics patch may also be worn during bathing, taking a shower or activities of sports. The at least one flexible protective layer, as an example, may comprise at least one foil. Additionally or alternatively, one or more protective layers may be applied by coating techniques, such as from the liquid phase, e.g. by spray coating, dispensing, printing or the like, followed e.g. by one or more drying or curing steps. Thus, as an example, one or more silicone materials may be applied and/or one or more epoxy materials.

As used herein, further, the term "upper side" generally refers to a side of the flexible electronics patch facing away from the skin of the user. Similarly and consequently, the term "lower side" may generally refer to a side of the flexible electronics patch facing the skin of the user, e.g. by directly or indirectly resting on the skin of the user.

As further used herein and in the following, the terms "first", "second", "third" and "fourth", as well as further numerals, generally, are used as nomenclature, only, without numbering and without ranking. Further layers elements may be present.

As further used herein, the term "adhesive layer" may generally refer to an amount of adhesive material. The amount of adhesive material may, e.g., fully or partially be embodied as a layer applied to at least one surface or may fully or partially be embodied as a free-standing film. The term "layer" may generally refer to an arbitrary amount of material, which may have an essentially flat shape. Alternatively, however, the "layer" may also comprise one or more dots of material. Thus, the term "adhesive layer", as used herein, may generally refer to an amount of adhesive, independent from the lateral extension thereof. As an example, the adhesive layer may comprise one or more amounts of adhesive, being formed in an essentially flat fashion, or may, additionally or alternatively, comprise one or more dots of the adhesive material.

The at least one first adhesive layer, as an example, may be applied directly or indirectly to the lower side of the flexible electronics patch. As an example, the at least one first adhesive layer may be applied as an adhesive directly onto a lower side of the substrate, facing towards the skin. Additionally or alternatively, however, the at least one first adhesive layer may also be provided on a separate element, such as on a plaster or adhesive strip, being located in between the substrate and the skin, with an adhesive side facing towards the skin, forming the at least one first adhesive layer.

The sensor system further comprises at least one applicator unit, in the following also simply referred to as an applicator, for applying the flexible electronics patch to the skin of the user. As used herein, the term "applicator unit" generally may refer to a device capable of applying the electronics path to the skin. The applicator unit, as an example, may simply comprise a handle and an element configured for holding the flexible electronics patch during transfer onto the skin of the user. The element configured for holding the flexible electronics patch, as an example, may simply be or may simply comprise a surface on which the flexible electronics patch may be located during transfer, e.g. by adhesive forces of the at least one second adhesive layer, as will be outlined in further detail below. Once the first adhesive layer adheres to the skin, the flexible electronics patch may dispatch from the applicator. Additionally, one or more holding elements may be present for holding the flexible electronics patch during transfer. Additionally and optionally, however, the at least one applicator unit may comprise further functionality, as will be outlined in further detail below. Thus, as an example, the at least one applicator may comprise at least one insertion device, e.g. an insertion device having at least one insertion needle, for inserting the at least one analyte sensor into the body tissue.

The sensor system further comprises at least one second adhesive layer for adhering the flexible electronics patch to the applicator unit before applying the flexible electronics patch to the skin of the user. The at least one second adhesive layer may be part of the at least one flexible electronics patch, may be part of the applicator unit or both, or may be provided as a separate adhesive layer. As an example, the second adhesive layer may be implemented in between the flexible electronics patch and the applicator unit in a state, in which the flexible electronics patch is still attached to the applicator unit, i.e. before and during application of the flexible electronics patch onto the skin. The second adhesive layer may be an adhesive layer applied to an upper side of the flexible electronics patch and/or to a lower side of the applicator unit. The second adhesive layer, as an example, may be provided by at least one plaster or the like.

In order to provide a transfer of the flexible electronics patch from the applicator unit onto the skin, the adhesive force of the second adhesive layer is lower than an adhesive force of the first adhesive layer, such that when the flexible electronics patch is pressed onto the skin by the applicator unit and the applicator unit is removed, the flexible electronics patch is separated from the applicator and adheres to the skin. The adhesive forces may simply be measured by applying and measuring a pulling force required for pulling off the flexible electronics patch from the skin and the pulling force required for pulling off the flexible electronics patch from the applicator unit, e.g. by using a simple spring balance. The above-mentioned setup with the adhesive force of the second adhesive layer between the flexible electronics patch and the applicator unit being lower than the adhesive force of the first adhesive layer between the flexible electronics patch and the skin may be adjusted by several means. Thus, as an example, the choice of adhesive may have an impact on the adhesive force. Thus, in the second adhesive layer, a different adhesive may be used as in the first adhesive layer, the adhesive of the second adhesive layer providing a lower adhesive force. Secondly, the thickness of the adhesive layers and/or the amount of adhesive used therein may be adjusted. As an example, for the second adhesive layer, a very thin adhesive layer may be used, having a lower thickness as compared to the thickness of the first adhesive layer. Further, other types of adhesive forces may be used which, on a molecular basis, provide different physical and/or chemical bonding forces. Further, additionally or alternatively, in order to provide differing adhesive forces, the contact area of the adhesive layer and/or the size of the adhesive layer and/or the amount of adhesive contained in the adhesive layer may be adjusted. Thus, as an example, in order to provide the adhesive force of the second adhesive layer being lower than the adhesive force of the first adhesive layer, the size of the second adhesive layer may be reduced as compared to the size of the first adhesive layer. Thus, as an example, the second adhesive layer may comprise one or more adhesive dots, whereas the first adhesive layer may comprise one or more adhesive patches.

Thus, as outlined above, the adhesive force of the first adhesive layer or of the second adhesive layer, or of further adhesive layers or adhesive elements or adhesives that may be described below, such as a third adhesive layer and a fourth adhesive layer, may be influenced or controlled by a size of the adhesive layer. Thus, as an example, the second adhesive layer may have a smaller size than the first adhesive layer to achieve or contribute to achieving that the adhesive force of the second adhesive layer may be smaller than the adhesive force of the first adhesive layer. In particular, the size of the adhesive layer may be reduced to one or several adhesive dots, such that the adhesive layer may comprise or may be implemented as one or several adhesive dots. However, the number of adhesive dots or the size of the adhesive layer may not correspond to the adhesive force of the adhesive layer. Thus, as an example, the first adhesive layer may be implemented as a smaller number of adhesive dots than the second adhesive layer, with the adhesive force of the first adhesive layer nevertheless exceeding the adhesive force of the second adhesive layer. As used herein, the term "dot" may generally refer to an arbitrarily shaped area, for instance a circular area, of small size, preferably of no more than 10 mm$^2$, more preferably of no more than 2 mm$^2$, most preferably of no more than 0.25 mm$^2$.

As outlined above, the flexible electronics patch comprises at least one flexible protective layer. As discussed above, various possibilities for providing the flexible protective layer exist. Thus, the flexible protective layer may comprise one or both of a plaster or an adhesive strip.

The flexible electronics patch specifically may have a sandwich setup, with the flexible circuit board sandwiched in between two or more layers. Thus, specifically, the sensor system may further comprise at least one flexible bottom layer. The flexible circuit board specifically may be located in between the flexible bottom layer and the flexible protective layer. The above-mentioned lower side which may have the first adhesive layer thereon specifically may be located on the flexible bottom layer. The first adhesive layer may be located on the lower side of the flexible bottom layer, for adhesion of the flexible bottom layer to the skin. The flexible bottom layer specifically may comprise one or both of a plaster or an adhesive strip.

As discussed above, for the second adhesive layer, various possibilities exist. Thus, the second adhesive layer may be located on at least one of a lower surface of the applicator facing towards the flexible electronics patch or an upper surface of the flexible electronics patch. Additionally or alternatively, at least one additional adhesive element may be provided in between the flexible electronics patch and the applicator unit.

The flexible circuit board specifically may be or may comprise at least one flexible printed circuit board. Thus, as an example, the flexible circuit board may be made by printing one or more electrically conductive inks onto the flexible substrate, thereby creating a conductive pattern.

The flexible circuit board specifically may have a thickness of 10 to 250 μm, preferably 50 to 100 μm. The flexible substrate specifically may comprise a flexible foil.

The flexible circuit board specifically may comprise at least one printed electronics component, the at least one printed electronics component being selected from the group consisting of: at least one printed conductive lead; at least one printed resistor; at least one printed antenna; at least one printed capacitor; at least one printed processor. The flexible circuit board further may comprise at least one contact pad for attachment of at least one electrical contact of the analyte sensor. The sensor system may further comprise at least one protective foil for covering the analyte sensor and the contact pad when the electrical contact of the analyte sensor is attached to the contact pad of the flexible circuit board. The at least one protective foil, as an example, may also be applied by the applicator unit, e.g. when the flexible electronics patch is applied onto the skin and/or when the analytical sensor is inserted into the body tissue. Thus, the applicator unit, as an example, may be configured for inserting the analyte sensor into the skin, attaching the at least one electrical contact of the analyte sensor to the at least one contact pad of the flexible circuit board and, subsequently, applying the at least one protective foil over the analyte sensor and the contact pad in the region in which the contact pad of the flexible circuit board electrically contacts the at least one electrical contact of the analyte sensor. As an example, the at least one protective foil may comprise at least one plastic foil, with or without an adhesive.

One or both of the flexible circuit board or the analyte sensor may comprise at least one sealing ring surrounding at least one contact region in which the at least one electrical contact of the analyte sensor is attached to the contact pad of the flexible circuit board. The sealing ring, as an example, may be provided by the analyte sensor, having the sealing ring surrounding its at least one electrical contact. The sealing ring, for example, may provide a protection of the at least one electrical contact and/or the at least one contact pad against moisture. The sealing ring, for example, may comprise at least one of an epoxy or a silicone. The sealing ring, besides providing protective properties, may also function as an adhesive, for adhering the analyte sensor to the flexible circuit board.

The at least one analyte sensor, as an example, may comprise at least one flexible analyte sensor shaft with at least one working electrode and at least one further electrode disposed thereon. The flexible analyte sensor shaft may be insertable through the skin, into the body tissue. The analyte sensor may further comprise at least one contact portion, the contact portion having the at least one electrical contact disposed thereon. The at least one electrical contact may be electrically connected with the at least one working electrode and the at least one further electrode.

The contact pad specifically may comprise at least one of a connector, a printed carbon pill or a conductive rubber. Other means for providing the contact pad are feasible, such as by simply providing a printed conductive patch, such as at least one rectangular, circular, round, oval or polygonal conductive patch.

As outlined above, the applicator may have one or more functionalities. As a main function, the applicator or applicator unit may function for transfer of the flexible electronics patch onto the skin of the user. Thus, the applicator unit may simply comprise or provide at least one of a grip or handle for pressing the flexible electronics patch onto the skin of the user. Additionally, however, the applicator unit may be configured for inserting the analyte sensor into the body tissue. The applicator unit therefore may comprise at least one insertion needle for inserting the analyte sensor into the body tissue. The at least one insertion needle, as an example, may comprise at least one cannula, for example a slotted cannula, having a tip and a lumen for receiving the analyte sensor during insertion. The applicator unit may further comprise at least one driving mechanism for driving the insertion needle into the body tissue. As an example, the at least one driving mechanism may comprise at least one spring for driving the insertion needle into the body tissue. Further, the driving mechanism may comprise at least one slider and/or at least one sliding system, along which or by which the insertion needle may be moved during insertion, specifically a linear sliding system.

The analyte sensor, in use, may be electrically connected with the flexible electronics patch in a wire bound or wireless fashion. In the first case, several scenarios exist. Thus, the analyte sensor may be permanently connected to the flexible electronics patch before, during and after insertion. Alternatively, however, the analyte sensor may be connected to the flexible electronics patch during or after insertion. Thus, as will be outlined in further detail below, the applicator unit may also be configured for electrically connecting the analyte sensor to the flexible electronics patch immediately before, during or after insertion. The sensor system specifically, before insertion of the analyte sensor into the body tissue, may be configured in a way selected from the group consisting of:

a first configuration, in which the analyte sensor is electrically connected to the flexible circuit board; or a second configuration, in which the analyte sensor is electrically disconnected from the flexible circuit board before insertion, and the driving mechanism is configured for electrically contacting at least one electrical contact of the analyte sensor with at least one contact pad of the flexible circuit board during insertion.

In case the second configuration is given, specifically, before insertion of the analyte sensor into the body tissue, the analyte sensor may be directly or indirectly attached to the applicator by at least one third adhesive layer. The at least one third adhesive layer may be located on one or both of the applicator or the analyte sensor or an element connected to the analyte sensor, such as a protective foil. The analyte sensor may comprise at least one fourth adhesive layer for attachment of the analyte sensor to the flexible circuit board during insertion. The at least one fourth adhesive layer may be located on one or both of the analyte sensor or the flexible circuit board. The fourth adhesive layer may have a higher adhesive force than the third adhesive, such that when the analyte sensor is attached to the flexible circuit board and the applicator is removed, the analyte sensor remains attached to the flexible circuit board, by the fourth adhesive layer. Thus, the third adhesive layer and the fourth adhesive layer, similar to the first and second adhesive layers discussed above, again may provide a transfer chain for transferring the analyte sensor from the applicator onto the flexible circuit board. For measuring the adhesive force, reference may be made to the measurement method discussed above. Further, for providing appropriate adhesive strength for the third and fourth adhesive layers, reference may also be made to the possibilities discussed above in the context of the first and second adhesive layers.

Specifically in case the second configuration is given, i.e. when the analyte sensor is transferred from the applicator unit onto the flexible electronics patch during insertion, the sensor system may further comprise at least one pressing element for pressing the at least one electrical contact of the analyte sensor onto the contact pad of the flexible circuit board after insertion. The at least one pressing element may be part of at least one of the flexible circuit board, the analyte sensor or of a third element, such as of the above-mentioned protective foil.

The flexible electronics patch, specifically the at least one flexible circuit board, further may have at least one opening, such that an insertion needle of the applicator may protrude through the flexible electronics patch into the body tissue. As an example, the opening may be a through hole extending through the full flexible electronics patch, from the upper side to the lower side. Alternatively, however, the opening may also be provided in a part of the flexible electronics patch, only. Thus, as an example, the opening may be provided in one or both of the flexible substrate or the flexible bottom layer, whereas no corresponding opening may be provided in the flexible protective layer. The opening may be located centrally within the flexible electronics patch or off-centered. Consequently, the analyte sensor may protrude from the flexible electronics patch in a centered or off-centered fashion.

As discussed above, for the at least one electronics component, various possibilities exist, which may also be combined. Thus, as an example, at least one passive electronic component and/or at least one active electronic component may be provided. The at least one electronics component specifically may comprise at least one component selected from the group consisting of: an application-specific integrated circuit; a potentiostat; a voltage measurement device; a current measurement device; a voltage source; a current source; a data transmitter for transmitting measurement data to at least one data reader. The at least one electronics component may be adhered to the flexible circuit board by at least one electrically conductive adhesive. Additionally or alternatively, however, as discussed above, soldering, bonding or welding techniques may be used.

The flexible electronics patch may further comprise at least one energy storage device, specifically at least one of a battery or an accumulator. The at least one energy storage device may comprise at least one of a rigid electronics element, specifically a coin cell, or a fully flexible battery. The latter, as an example, may be provided by integrating and/or attaching at least one foil-type battery to the flexible electronics patch, e.g. next to the substrate, on top of the substrate or below the substrate. Thus, the at least one energy storage device may comprise a fully flexible battery. The fully flexible battery may be arranged above or below the flexible circuit board.

The flexible electronics patch specifically may be configured for wireless communication and/or for wire-bound communication with at least one further device, e.g. with at least one data reader. The communication may, as an example, take place via nearfield standard (NFC), via Bluetooth or via other types of wireless communication. For wireless communication and/or for receiving energy from a further device in a wireless fashion, the flexible electronics patch specifically may comprise at least one antenna. Thus, the at least one flexible electronics patch may comprise at least one antenna for one or both of sending or receiving information. The antenna, as an example, may be or may comprise a flat, printed conductive pattern, e.g. printed onto the substrate answers or another component of the flexible electronics patch, such as the flexible protective layer and/or the flexible bottom layer and/or at least one additional layer above or below the substrate.

The at least one optional antenna and the at least one optional energy storage device may be arranged taking into account that typical energy storage devices exert a shielding effect for electromagnetic waves. Thus, as an example, the at least one antenna may be located next to the energy storage device, such that an emission of electromagnetic waves in both directions is possible. Alternatively, in a sandwich fashion, the at least one antenna may comprise at least one first antenna located above the energy storage device and at least one antenna located below the energy storage device. Additionally or alternatively, as discussed above, the at least one antenna may also fully or partially be located next to at least one energy storage device.

In a further aspect of the present invention, a method of manufacturing a flexible electronics patch for use in a sensor system according to the present invention is disclosed. For potential embodiments of the flexible electronics patch, which also pertain to the method, reference may be made to the description given above or given in further detail below. The method comprises the following steps. The method steps may be performed in the given order. Still, a different order is also feasible. Further, two or more of the method steps may also be performed simultaneously or in a timely overlapping fashion. Further, one, two, more than two or even all of the method steps may be performed once or repeatedly.

The method comprises the following steps:
a) providing at least one flexible circuit board having a flexible substrate and a plurality of conductive paths on the flexible substrate;
b) providing at least one electronics component for performing at least one analyte measurement using at least one analyte sensor;
c) assembling the electronics component with the flexible circuit board, by one or both of attaching the electronics component to the flexible circuit board or integrating the electronics component into the flexible circuit board;
d) providing at least one flexible protective layer;
e) at least partially covering an upper side of the flexible circuit board with the protective layer; and
f) providing at least one first adhesive layer on a lower side of the flexible electronics patch, configured for adhering the flexible electronics patch to the skin of the user.

For providing the plurality of conductive paths on the flexible substrate, specifically, at least one printing technique may be used, such as flexo printing or offset printing. One or more conductive materials may be used, e.g. electrically conductive inks. Still, other techniques may be used, such as standard galvanic techniques and/or etching techniques.

For providing the at least one electronics component and for assembling the same with the flexible circuit board, assembly techniques known from electronics manufacturing may be used. As an example, flip chip techniques may be used, specifically by using electrically conductive inks or adhesives. Further, mass manufacturing techniques such as pick and place techniques may be used.

For providing the at least one flexible protective layer, as discussed above, various possibilities exist which may also be combined. Thus, as an example, the at least one protective layer may be applied in a liquid form, followed by at least one drying or curing step. Additionally or alternatively, the at least one protective layer may also be applied in the form of at least one protective foil or plaster which may be placed on top of the flexible circuit board.

Similarly, depending on the nature of the at least one first adhesive layer on the lower side of the flexible electronics patch, various possibilities exist. Thus, as an example, a spray coating or liquid coating with at least one adhesive may take place. Additionally or alternatively, at least one adhesive plaster may be applied to the lower side of the flexible electronics patch, specifically to the lower side of the substrate.

In case the at least one second adhesive layer is also part of the flexible electronics patch, the method may further comprise applying the at least one second adhesive layer to an upper side of the flexible electronics patch. Again, the supplication of the at least one second adhesive layer may comprise an application in a liquid form or an application as a separate element, e.g. an adhesive foil.

In a further aspect of the present invention, a method of manufacturing a sensor system according to the present invention is disclosed. For potential details of the sensor system, reference may be made to the description given above or given in further detail below. The method comprises the following steps. The method steps may be performed in the given order. Still, a different order is also feasible. Further, two or more of the method steps may also be performed simultaneously or in a timely overlapping fashion. Further, one, two, more than two or even all of the method steps may be performed once or repeatedly.

The method comprises the following steps:
i. manufacturing at least one flexible electronics patch by using the method according to the present invention, as disclosed above or as disclosed in further detail below;
ii. providing at least one applicator unit for applying the flexible electronics patch to the skin of the user;
iii. providing at least one second adhesive layer; and
iv. adhering the flexible electronics patch to the applicator unit by using the second adhesive layer.

As discussed above, the at least one second adhesive layer may be provided on one or both of the applicator unit or the flexible electronics patch or may be provided as a separate element, e.g. by providing a separate adhesive foil. The applicator unit, for adhering the flexible electronics patch to the applicator unit, may comprise at least one flat or curved bottom surface onto which the flexible electronics patch may be applied. Other means, however, are feasible.

The sensor system and the methods of manufacturing according to the present invention provide a large number of advantages over known devices and methods. Thus, as discussed above, in typical continuous monitoring systems, specifically for glucose monitoring, as well as for medication pumps, flexible circuit boards are used, having active electrical circuits with voluminous batteries. These circuit boards, typically, are located in housings, being made of rigid materials and typically being composed of a plurality of components. The rigid patches, typically, are mounted by using flexible plasters. By the combination of the rigid patch and the flexible plaster, the comfort of wearing as well as the duration of use is typically limited. According to the present invention, contrarily, patches having the same or similar functionality may be created, which may be realized by using thin foils as a flexible substrate may be used. The flexible substrate, as an example, may be bendable and even elastic or extendable. The batteries or energy storage devices, as discussed above, may also be realized by using flexible batteries and/or by using printing technologies. Consequently, the setup of the flexible electronics patch may be realized in such a way that the flexible electronics patch adjusts to the body in each situation, which significantly increases the comfort of wearing. Further, the flexible electronics patch may even be worn in locations of the human body which, so far, may not be used by rigid patches. Further, the duration of use may be increased significantly, specifically since the problem of a rigid patch detaching from the flexible skin by mechanical tension may significantly be reduced.

The flexible substrate may be realized as an ultra thin, flexible foil, having conductive traces thereon. The flexible substrate may even be made of an elastic or even extendable material. The extension may take place in any dimension and/or direction in space. Flexible or even elastic foils are available, which are extendable by 20% or even more. Even in a folded or crumpled state, the foils may maintain their functionality. Further, the flexible substrate may also be made out of a material which is permeable for water and moisture, if required. Thereby, an evaporation of water from the skin is still possible, which may increase the comfort of wearing. Further, if required, the flexible substrate, specifically ultra thin foils, may be partially stiffened or may be combined in a multi-layer setup, in order to obtain desired mechanical and/or chemical properties.

The at least one electronics component and/or the conductive paths may be realized by using various techniques. Thus, active electronic devices may directly be realized by using flexible substrates, by directly applying the electronics devices onto the flexible substrate. Further, active electronics devices may directly be printed onto the flexible substrate and/or onto flexible, extendable foils. In this context, technical developments in the field of printable electronics, which were made over the most recent years, may be applied.

For providing the conductive paths on the flexible substrate, as discussed above, printable inks, such as silver-based printable inks, and commercially available printing systems, such as ink-jet printing or real-to-real manufacturing techniques, may be used and may be applied in an industrial environment. Inks for the conductive traces and paths on the flexible substrate may be applied in a very thin manner and, thus, may sustain an extension of the substrate and/or a bending or even crumbling of the flexible substrate, without losing their electrical functionality. Specifically, no electrical interruption and/or change of a resistance may take place during bending or crumbling.

The at least one electronics component, as an example, may be applied by conventional assembling techniques. As an example, pick-and-place technology, e.g. as typically used for SMD assembly, may be used. Passive and/or active electronics components may be mounted by using adhesives, wherein an electrical connection may take place by using flexible electrically conductive adhesives. Larger elements, such as ASICs and/or data storage devices, may be secured additionally, e.g. by placing a rim of adhesive at the edge of the devices.

The use of extendable and flexible ultra thin foils may provide an elasticity and/or an elasticity module which are similar to the properties of the human skin or even exceed the properties of the human skin. Extendable ultra thin foils may also be used as carriers for conductive paths and/or may be implemented fully or partially into a flexible plaster. Thus, the flexible substrate and the plaster for adhering the flexible electronics patch may be realized as separate components and/or may fully or partially be integrated into one another.

As discussed above, by using permeable substrates, having a permeability for water vapor, the duration of use of the flexible electronics patch may be increased as compared to conventional rigid plasters and patches. Further, the setup on the human skin, using the flexible electronics patch, may be realized having a significantly reduced height, as compared to conventional rigid patches having a rigid housing. By reducing the height of the flexible electronics patch, the risk of the user accidentally stripping off the flexible electronics patch may significantly be reduced. Further, by using a flat, flexible electronics patch, the comfort of wearing is increased, specifically when the user rests on the patch, e.g. during sleeping, sitting or wearing tight clothes. The duration of wearing on the skin may be increased as compared to thick, rigid patches.

On the conductive paths of the flexible circuit board, electronic devices and circuits may be applied. The electronics devices, as an example, may be mounted onto partially stiffened and/or non-flexible regions of the flexible substrate. Thus, in general, the flexible substrate may provide flexible properties in one or more regions, but, optionally, may also have one or more non-flexible regions, e.g. regions which artificially are stiffened by applying stiff elements. The remainder of the flexible substrate, e.g. at least 40% of the substrate, more preferably at least 50% or at least 70% of the flexible substrate, may provide flexible properties. The stiff regions of the flexible electronics patch, however, may be significantly reduced as compared to conventional patches. As discussed above, communication between the flexible electronics patch and the sensor and/or another device, e.g. a readout device, specifically may take place in a wireless fashion. One or more antennae can be applied onto the flexible substrate and/or onto another part of the flexible electronics patch, as a flat conductive element. As an example, the at least one flexible electronics patch may comprise at least one RFID antenna and/or at least one NFC antenna.

An isolation against the environment may take place via the at least one protective layer and/or via the at least one flexible bottom layer. A multi-layer foil setup generally may be realized in a very small and thin fashion. As discussed above, the at least one protective layer may either be realized by using one or more foils or, additionally or alternatively, may be realized by corresponding coatings, e.g. a parylene coating.

The increased flexibility as compared to conventional patches for analytical sensors may, as discussed above, also open up possibilities for other applications. Thus, specifically, the location of applying the flexible electronics patch to the human body may be varied. As an example, the flexible electronics patch may also be applied to new locations on the human body, which, typically, undergo a larger extension of the human skin as compared to the upper arm or the lower side of the human belly. Due to the possibility of manufacturing the flexible electronics patch in a very flat fashion, the flexible electronics patch may also be applied in regions of the human body which typically are in contact with a chair or a mattress when sitting or sleeping. Other locations on the human body are accessible for application in which protruding patches generally are disadvantages, due to the risk of being torn off the human body and/or due to the discomfort of pressure exerted by voluminous, rigid patches.

The ultra thin foils, as e.g. usable for the flexible substrate, may directly or indirectly be covered with at least one adhesive. Thus, the flexible substrate itself may also be used as an adhesive flexible substrate, e.g. by applying the first and/or second adhesive layer directly to the substrate. Additional adhesive plasters, thus, may be left out. Thus, the flexible circuit board, with the conductive paths and the at least one electronics component applied thereon, may directly be adhered to the human body. Further, the adhesive force of the first adhesive layer on the lower side of the flexible electronics patch, e.g. on the lower side of the flexible substrate, may be rendered in a less aggressive fashion, since the overall setup of the flexible electronics patch may be rendered very small and thin. By designing the flexible electronics patch rather flat and thin, the lever action of the flexible electronics patch may be reduced as compared to rigid electronics patches. Consequently, for the first adhesive layer, a lower adhesive force is generally required in order to keep the flexible electronics patch on the skin. Further, by using flexible foils, lower shear forces may occur as compared to the situation in rigid electronics patches.

Summarizing the findings of the present invention, the following embodiments are preferred:

Embodiment 1

A sensor system, comprising
at least one analyte sensor configured for at least partial implementation into a body tissue of a user;
at least one flexible electronics patch, the flexible electronics patch comprising
  at least one flexible circuit board having a flexible substrate and a plurality of conductive paths on the flexible substrate;
  at least one electronics component for performing at least one analyte measurement using the analyte sensor, the electronics component being one or both of attached to or integrated into the flexible circuit board;
  at least one flexible protective layer, the protective layer at least partially covering an upper side of the flexible circuit board; and
  at least one first adhesive layer on a lower side of the flexible electronics patch, configured for adhering the flexible electronics patch to the skin of the user;
at least one applicator unit for applying the flexible electronics patch to the skin of the user; and
at least one second adhesive layer for adhering the flexible electronics patch to the applicator unit before applying the flexible electronics patch to the skin of the user.

Embodiment 2

The sensor system according to the preceding embodiment, wherein an adhesive force of the second adhesive layer is lower than an adhesive force of the first adhesive layer, such that when the flexible electronics patch is pressed onto the skin by the applicator unit and the applicator unit is removed, the flexible electronics patch is separated from the applicator unit and adheres to the skin.

Embodiment 3

The sensor system according to any one of the preceding embodiments, wherein the flexible protective layer comprises one or both of a plaster or an adhesive strip.

Embodiment 4

The sensor system according to any one of the preceding embodiments, wherein the sensor system further comprises at least one flexible bottom layer, wherein the flexible circuit board is located in between the flexible bottom layer and the flexible protective layer.

Embodiment 5

The sensor system according to the preceding embodiment, wherein the lower side is located on the flexible bottom layer, wherein the first adhesive layer is located on the lower side of the flexible bottom layer, for adhesion of the flexible bottom layer to the skin.

Embodiment 6

The sensor system according to any one of the two preceding embodiments, wherein the flexible bottom layer comprises one or both of a plaster or an adhesive strip.

Embodiment 7

The sensor system according to any one of the preceding embodiments, wherein the second adhesive layer is located on at least one of a lower surface of the applicator unit facing towards the flexible electronics patch or an upper surface of the flexible electronics patch.

Embodiment 8

The sensor system according to any one of the preceding embodiments, wherein the flexible circuit board is a flexible printed circuit board.

Embodiment 9

The sensor system according to any one of the preceding embodiments, wherein the flexible circuit board has a thickness of 10 to 250 µm, preferably 50 to 100 µm.

Embodiment 10

The sensor system according to any one of the preceding embodiments, wherein the flexible substrate comprises a flexible foil.

Embodiment 11

The sensor system according to any one of the preceding embodiments, wherein the flexible circuit board comprises at least one printed electronics component, the at least one printed electronics component being selected from the group consisting of: at least one printed conductive lead; at least one printed resistor; at least one printed antenna; at least one printed capacitor; at least one printed processor.

Embodiment 12

The sensor system according to any one of the preceding embodiments, wherein the flexible circuit board comprises at least one contact pad for attachment of at least one electrical contact of the analyte sensor.

Embodiment 13

The sensor system according to the preceding embodiment, wherein the sensor system further comprises at least one protective foil for covering the analyte sensor and the contact pad when the electrical contact of the analyte sensor is attached to the contact pad of the flexible circuit board.

Embodiment 14

The sensor system according to any one of the two preceding embodiments, wherein one or both of the flexible circuit board or the analyte sensor comprise at least one sealing ring surrounding at least one contact region in which the at least one electrical contact of the analyte sensor is attached to the contact pad of the flexible circuit board.

Embodiment 15

The sensor system according to any one of the three preceding embodiments, wherein the at least one analyte sensor comprises at least one flexible analyte sensor shaft with at least one working electrode and at least one further electrode disposed thereon, the flexible analyte sensor shaft being insertable into the body tissue, the analyte sensor further comprising at least one contact portion, the contact portion having the at least one electrical contact disposed thereon, the at least one electrical contact being electrically connected with the at least one working electrode and the at least one further electrode.

Embodiment 16

The sensor system according to any one of the four preceding embodiments, wherein the contact pad comprises at least one of a connector, a printed carbon pill or a conductive rubber.

Embodiment 17

The sensor system according to any one of the preceding embodiments, wherein the applicator unit comprises at least one of a grip or handle for pressing the flexible electronics patch onto the skin of the user.

Embodiment 18

The sensor system according to any one of the preceding embodiments, wherein the applicator unit comprises at least one insertion needle for inserting the analyte sensor into the body tissue.

Embodiment 19

The sensor system according to the preceding embodiment, wherein the applicator unit further comprises at least one driving mechanism for driving the insertion needle into the body tissue.

Embodiment 20

The sensor system according to any one of the two preceding embodiments, wherein the sensor system, before insertion of the analyte sensor into the body tissue, is configured in a way selected from the group consisting of:
- a first configuration, in which the analyte sensor is electrically connected to the flexible circuit board; or
- a second configuration, in which the analyte sensor is electrically disconnected from the flexible circuit board before insertion, and the driving mechanism is configured for electrically contacting at least one electrical contact of the analyte sensor with at least one contact pad of the flexible circuit board during insertion.

Embodiment 21

The sensor system according to the preceding embodiment, with the proviso that the second configuration is given, wherein, before insertion of the analyte sensor into the body tissue, the analyte sensor is attached to the applicator unit by at least one third adhesive layer.

Embodiment 22

The sensor system according to the preceding embodiment, wherein the analyte sensor comprises at least one fourth adhesive layer for attachment of the analyte sensor to the flexible circuit board during insertion, wherein the fourth adhesive layer has a higher adhesive force than the third adhesive layer, such that when the analyte sensor is attached to the flexible circuit board and the applicator unit is removed, the analyte sensor remains attached to the flexible circuit board.

Embodiment 23

The sensor system according to any one of the three preceding embodiments, with the proviso that the second configuration is given, wherein the sensor system further comprises at least one pressing element for pressing the at least one electrical contact of the analyte sensor onto the contact pad of the flexible circuit board after insertion.

Embodiment 24

The sensor system according to any one of the preceding embodiments, wherein the flexible electronics patch, specifically the at least one flexible circuit board, has at least one opening, such that an insertion needle of the applicator unit may protrude through the flexible electronics patch into the body tissue.

Embodiment 25

The sensor system according to any one of the preceding embodiments, wherein the at least one electronics component comprises at least one component selected from the group consisting of: an application-specific integrated circuit; a potentiostat; a voltage measurement device; a current measurement device; a voltage source; a current source; a data transmitter for transmitting measurement data to at least one data reader.

Embodiment 26

The sensor system according to any one of the preceding embodiments, wherein the at least one electronics component is adhered to the flexible circuit board by at least one electrically conductive adhesive.

Embodiment 27

The sensor system according to any one of the preceding embodiments, wherein the flexible electronics patch further comprises at least one energy storage device, specifically at least one of a battery or an accumulator.

Embodiment 28

The sensor system according to the preceding embodiment, wherein the at least one energy storage device comprises at least one of a rigid electronics element, specifically a coin cell, or a fully flexible battery.

Embodiment 29

The sensor system according to the preceding embodiment, wherein the at least one energy storage device comprises a fully flexible battery, wherein the fully flexible battery is arranged above or below the flexible circuit board.

Embodiment 30

The sensor system according to any one of the preceding embodiments, wherein the at least one flexible electronics patch comprises at least one antenna for one or both of sending or receiving information.

Embodiment 31

The sensor system according to the preceding embodiment, wherein the at least one antenna comprises at least one first antenna located above an energy storage device and at least one second antenna located below the energy storage device.

Embodiment 32

The sensor system according to any one of the two preceding embodiments, wherein the at least one antenna is located next to the at least one energy storage device.

Embodiment 33

A method of manufacturing a flexible electronics patch for use in a sensor system according to any one of the preceding embodiments, the method comprising the following steps:
a) providing at least one flexible circuit board having a flexible substrate and a plurality of conductive paths on the flexible substrate;
b) providing at least one electronics component for performing at least one analyte measurement using at least one analyte sensor;
c) assembling the electronics component with the flexible circuit board, by one or both of attaching the electronics component to the flexible circuit board or integrating the electronics component into the flexible circuit board;
d) providing at least one flexible protective layer;
e) at least partially covering an upper side of the flexible circuit board with the protective layer; and
f) providing at least one first adhesive layer on a lower side of the flexible electronics patch, configured for adhering the flexible electronics patch to the skin of the user.

Embodiment 34

A method of manufacturing a sensor system according to any one of the preceding embodiments referring to a sensor system, the method comprising:
i. manufacturing at least one flexible electronics patch by using the method according to the preceding claim;
ii. providing at least one applicator unit for applying the flexible electronics patch to the skin of the user;
iii. providing at least one second adhesive layer; and
iv. adhering the flexible electronics patch to the applicator unit by using the second adhesive layer.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 6:
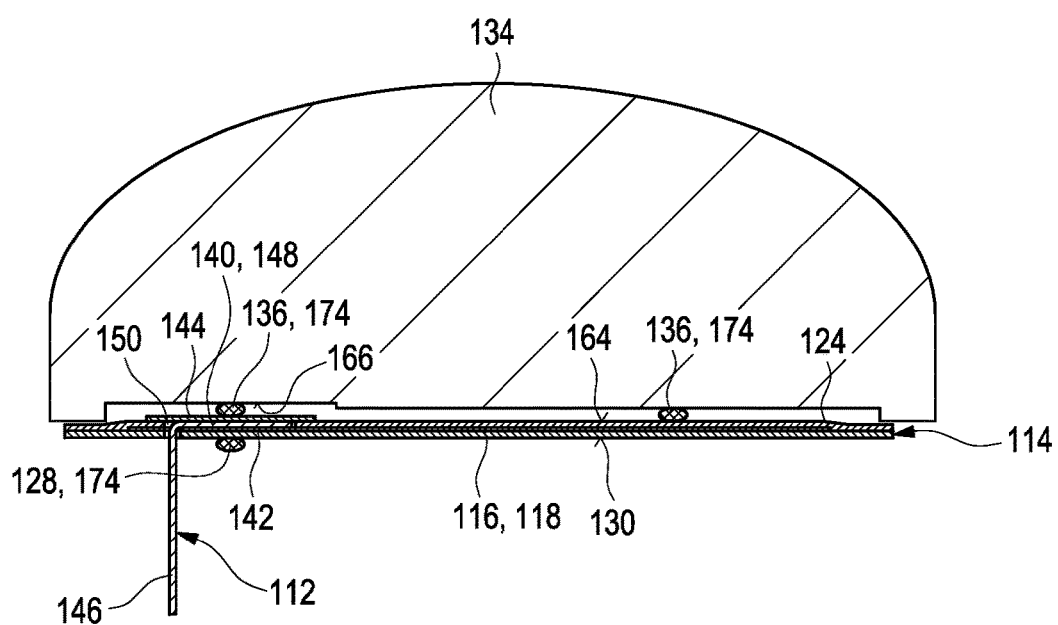
Figure 7:
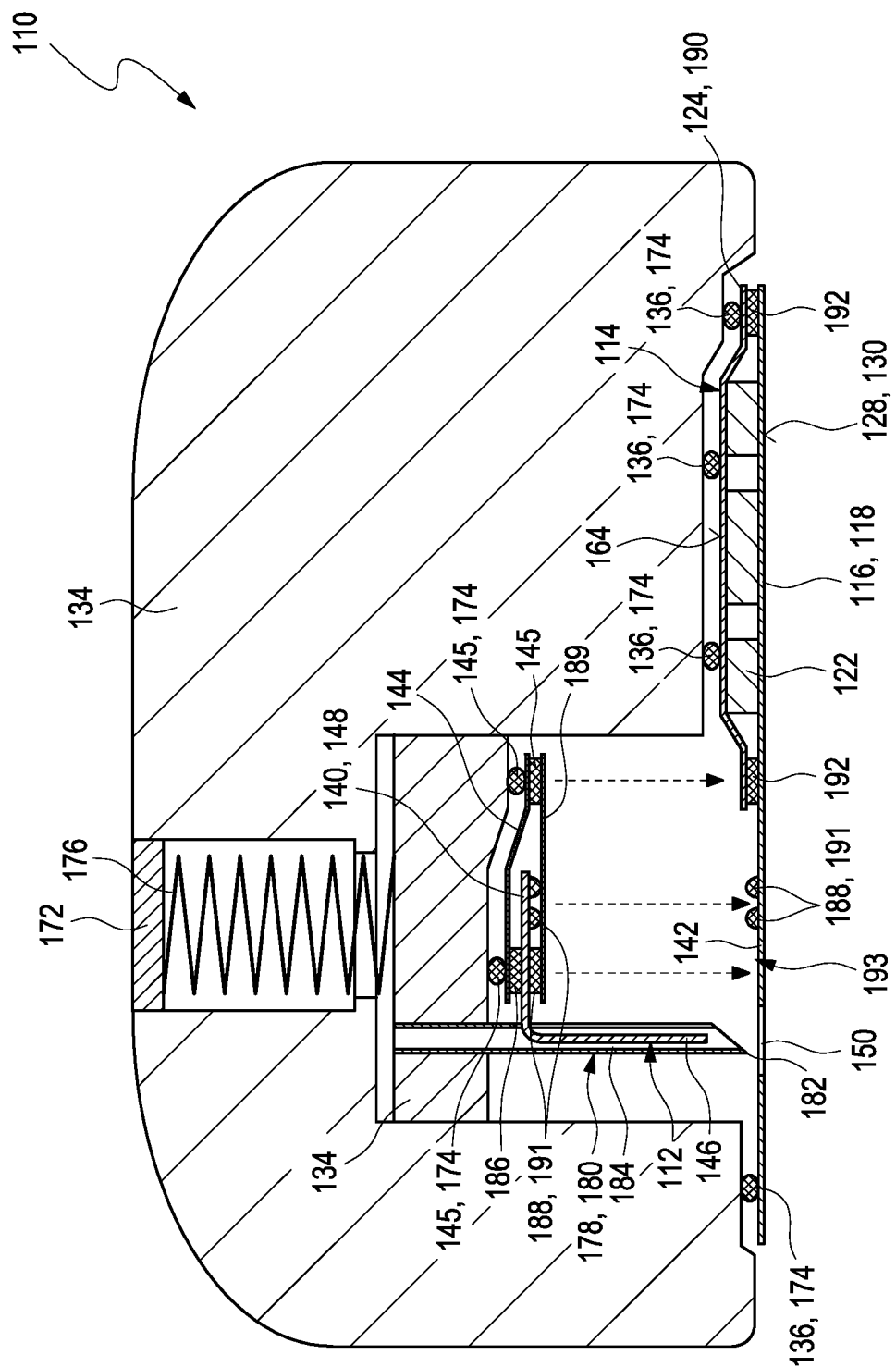
Figure 8:
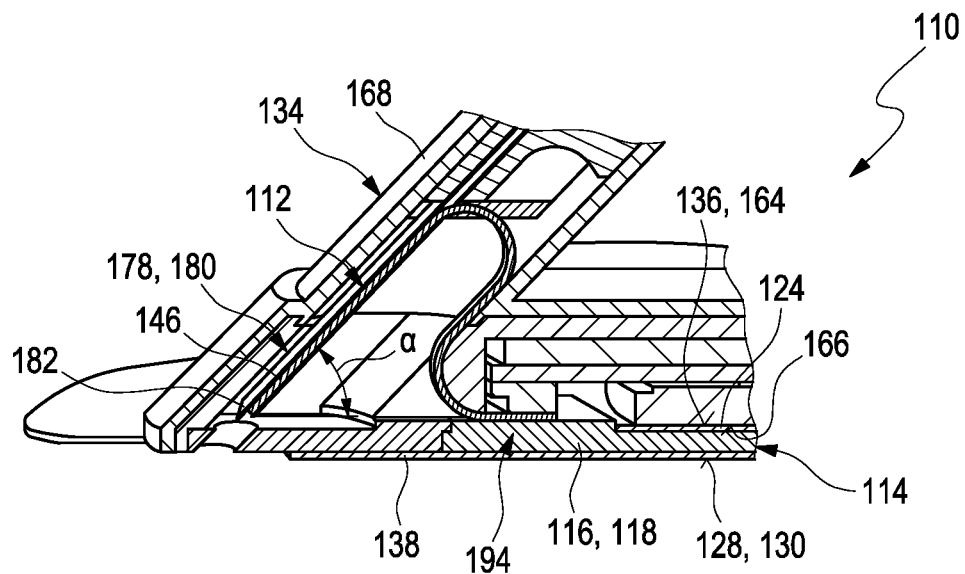
Figure 9:
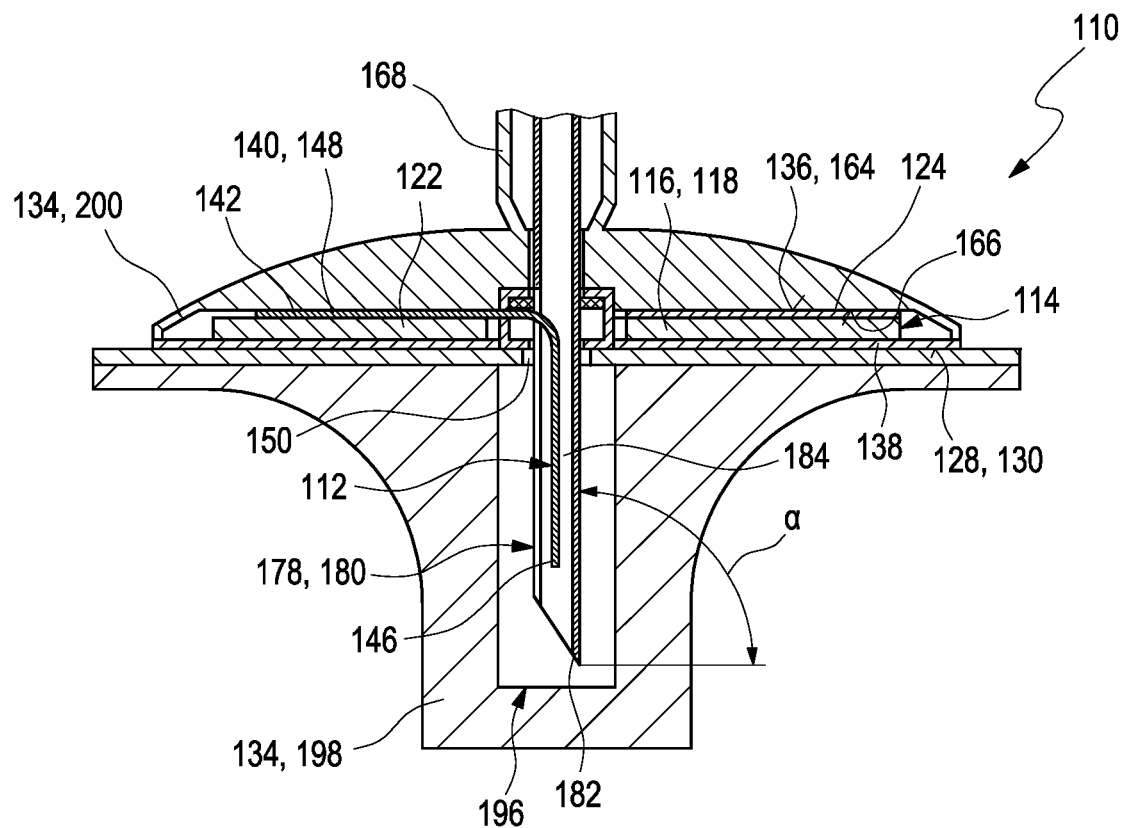
Figure 10:
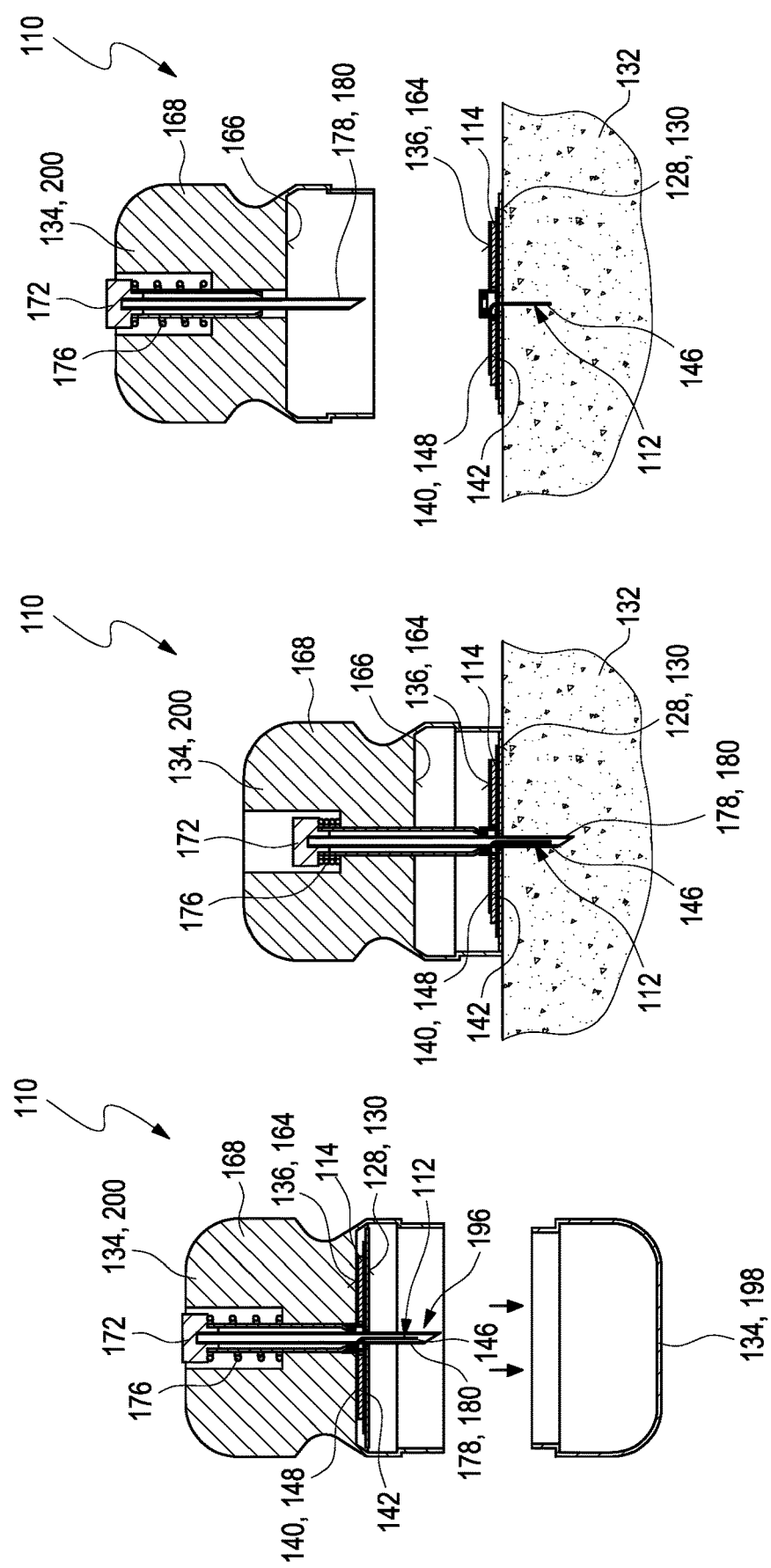
Figure 11:
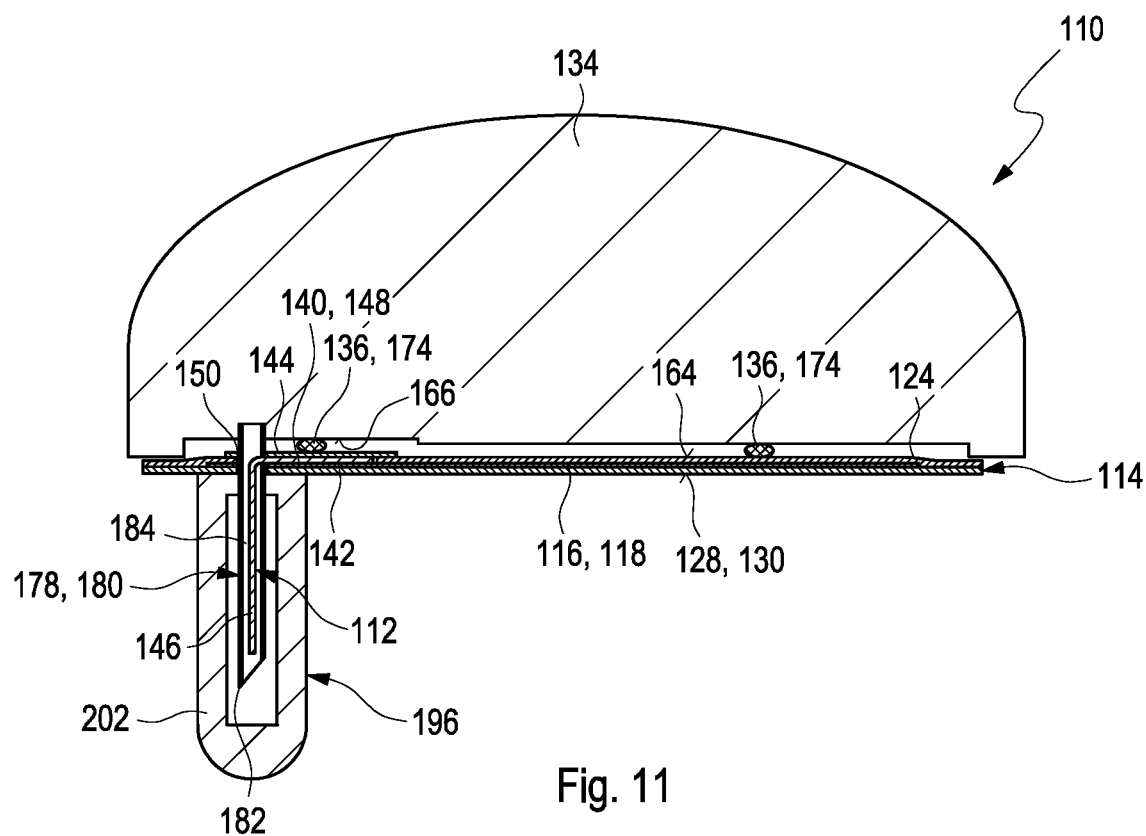
Figure 12:
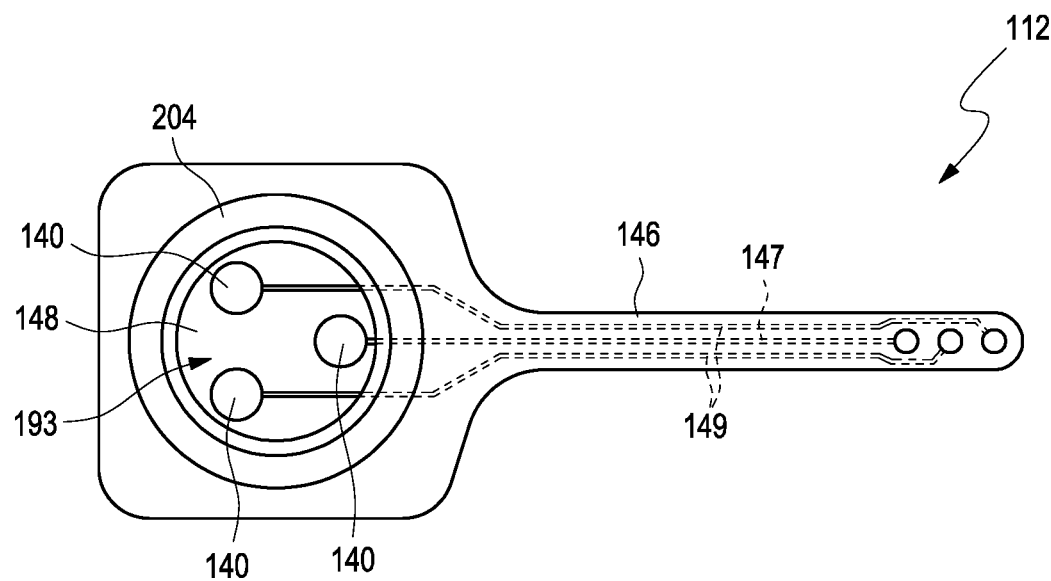

In the Figures:
FIG. 1 shows a partial view of an embodiment of a sensor system according to the present invention comprising a flexible bottom layer;
FIGS. 2A to 3B show two embodiments of an analyte sensor and a flexible electronics patch in a top view (FIGS. 2A and 3A) and a cross-sectional view (FIGS. 2B and 3B) each;
FIGS. 4A to 5B show two further embodiments of the sensor system from different perspectives with particular attention paid to an applicator unit;
FIGS. 6 and 7 show cross-sectional views of two further embodiments of the sensor system with particular attention paid to adhesive layers of the analyte system;
FIG. 8 shows a partial view of a cross-section of a further embodiment of the sensor system, with the analyte sensor being electrically connect to a flexible circuit board;
FIGS. 9 to 11 show cross-sectional views of three further embodiments of the sensor system with particular attention paid to a sterile assembly and an insertion mechanism;
FIG. 12 shows a top view of a further embodiment of an analyte sensor and a flexible electronics patch with particular attention paid to a sealing ring; and
FIGS. 13 to 15B shows five further embodiments of a sensor system in a cross-sectional view (FIG. 13) and in a partial view (FIGS. 14A to 15B) with particular attention paid to establishing and/or maintaining a connection between at least one electrical contact of the analyte sensor with at least one contact pad of the flexible circuit board by a pressing element.

DETAILED DESCRIPTION OF THE EMBODIMENTS

FIG. 1 shows a sensor system 110 according to the present invention in a partial view. The sensor system 110 comprises at least one analyte sensor 112 configured for at least partial implementation into a body tissue of a user. The sensor system 110 further comprises at least one flexible electronics patch 114. The flexible electronics patch 114 comprises at least one flexible circuit board 116 having a flexible substrate 118 and a plurality of conductive paths 120 on the flexible substrate 118. The flexible electronics patch 114 further comprises at least one electronics component 122 for performing at least one analyte measurement using the analyte sensor 112. The electronics component 122 is one or both of attached to or integrated into the flexible circuit board 116. The flexible electronics patch 114 further comprises at least one flexible protective layer 124. The protective layer 124 at least partially covers an upper side 126 of the flexible circuit board 116. The flexible electronics patch 114 further comprises at least one first adhesive layer 128 on a lower side 130 of the flexible electronics patch 114 configured for adhering the flexible electronics patch 114 to the skin 132 of the user. The sensor system 110 may further comprise at least one flexible bottom layer 138. The flexible circuit board 116 may be located in between the flexible bottom layer 138 and the flexible protective layer 124, as shown in FIG. 1. In such an embodiment the lower side 130 of the flexible electronics patch 114 may be located on the flexible bottom layer 138 and the first adhesive layer 128 may be located on the lower side 130 of the flexible bottom layer 138, for adhesion of the flexible bottom layer 138 to the skin of the user, as shown in FIG. 1. In particular, the flexible bottom layer 138 may comprise one or both of a plaster 190 or an adhesive strip. The sensor system 110 further comprises at least one applicator unit 134 (not shown in the partial view of the sensor system 110 depicted in FIG. 1) for applying the flexible electronics patch 114 to the skin 132 of the user. The sensor system 110 further comprises at least one second adhesive layer 136 for adhering the flexible electronics patch 114 to the applicator unit 134 before applying the flexible electronics patch 114 to the skin 132 of the user.

The sensor system 110 comprises at least one analyte sensor 112 configured for at least partial implementation into the body tissue of the user. The analyte sensor 112 may comprise at least one electrical contact 140 configured to be attached to a contact pad 142 of the flexible circuit board 116, as indicated by the dotted line in FIG. 1. The sensor system 110 may further comprise at least one protective foil 144, as depicted in FIG. 1, for covering the analyte sensor 112 and the contact pad 142, when the electrical contact 140 of the analyte sensor 112 is attached to the contact pad 142 of the flexible circuit board 116. The protective foil 144 may comprise an adhesive 145. The analyte sensor 112 may further comprise at least one flexible analyte sensor shaft 146, as shown in FIG. 1, with at least one working electrode 147 and at least one further electrode 149 disposed thereon (not shown in FIG. 1), the flexible analyte sensor shaft 146 being insertable into the body tissue. The analyte sensor 112 may further comprise at least one contact portion 148, the contact portion 148 having the at least one electrical contact 140 disposed thereon as illustrated in FIG. 1. The at least one electrical contact 140 may be electrically connected with the at least one working electrode and the at least one further electrode. The contact pad 142 may comprise at least one of a connector, a printed carbon pill or a conductive rubber. The at least one analyte sensor 112 is configured for at least partial implementation into the body tissue of the user. Thus, the flexible electronics patch 114, specifically the at least one flexible circuit board 116, may have at least one opening 150. As depicted in FIG. 1, specifically, the flexible protective layer 124 and the flexible bottom layer 138 may also have at least one opening 150, to facilitate the at least partial implementation of the analyte sensor 112 into the body tissue of the user. The opening 150 may in particular allow for an insertion needle 152, shown for example in FIGS. 7 to 11 and FIG. 13, to protrude through the flexible electronics patch 114 into the body tissue.

The sensor system 110, in particular the flexible electronics patch 114, comprises at least one flexible circuit board 116. In particular the flexible circuit board 116 may be a flexible printed circuit board 116. Further, the flexible circuit board 116 may have a thickness of 10 to 250 µm, preferably 50 to 100 µm. Furthermore, the flexible circuit board 116 may comprise at least one printed electronics component 154 selected from the group consisting of: at least one printed conductive lead, as shown in FIG. 1; at least one printed resistor; at least one printed antenna; at least one printed capacitor; at least one printed processor. The flexible circuit board 116 further comprises a flexible substrate 118. Specifically the flexible substrate 118 may comprise a flexible foil 158, as illustrated in FIG. 1. The flexible electronics patch 114 comprises at least one electronics component 122. The at least one electronics component 122 may comprise at least one component selected from the consisting of: application-specific integrated circuit 159, as illustrated in FIG. 1; a potentiostat; a voltage measurement device; a current measurement device; a voltage source; a current source; a data transmitter for transmitting measurement data to at least one data reader. The at least one electronics component 122 may be adhered to the flexible circuit board by at least one electrically conductive adhesive.

The flexible electronics patch 114 may in particular comprise at least one energy storage device (not shown in the Figures), specifically at least one of a battery or an accumulator. The at least one energy storage device may comprise at least one of a rigid electronics element, specifically a coin cell, or a fully flexible battery The fully flexible battery may be arranged above or below the flexible circuit board 116. In particular, the fully flexible battery may be part of the flexible bottom layer 138. The at least one flexible electronics patch 114 may further comprise at least one antenna (not shown in the Figures) for one or both of sending or receiving information. In particular, the antenna may comprise at least one first antenna located above the energy storage device and at least one second antenna located below the energy storage device. Specifically, the at least one antenna may be located next to the at least one energy storage device.

Figure 2:
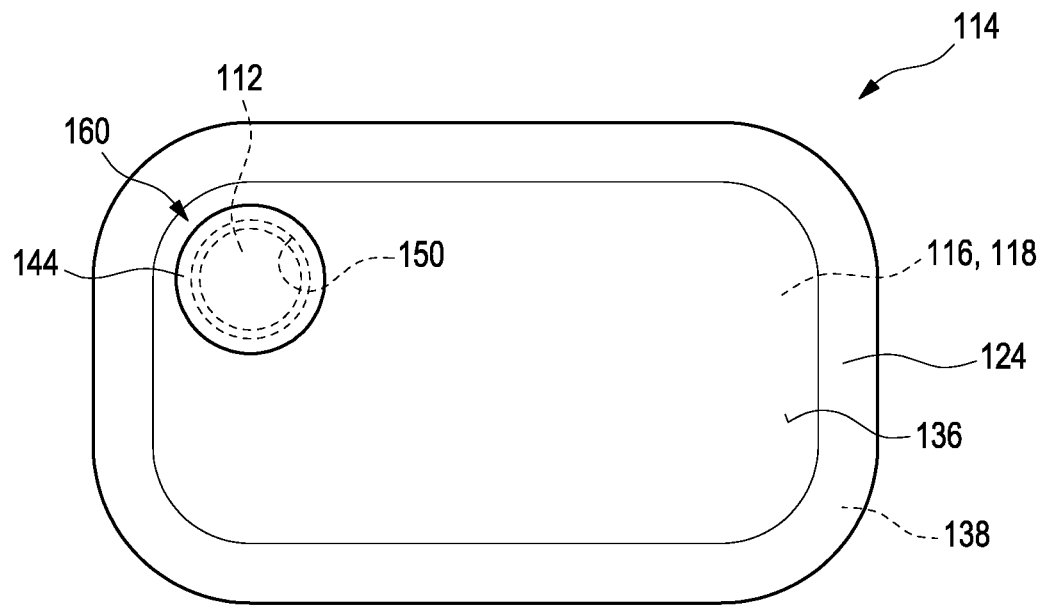
Figure 2:
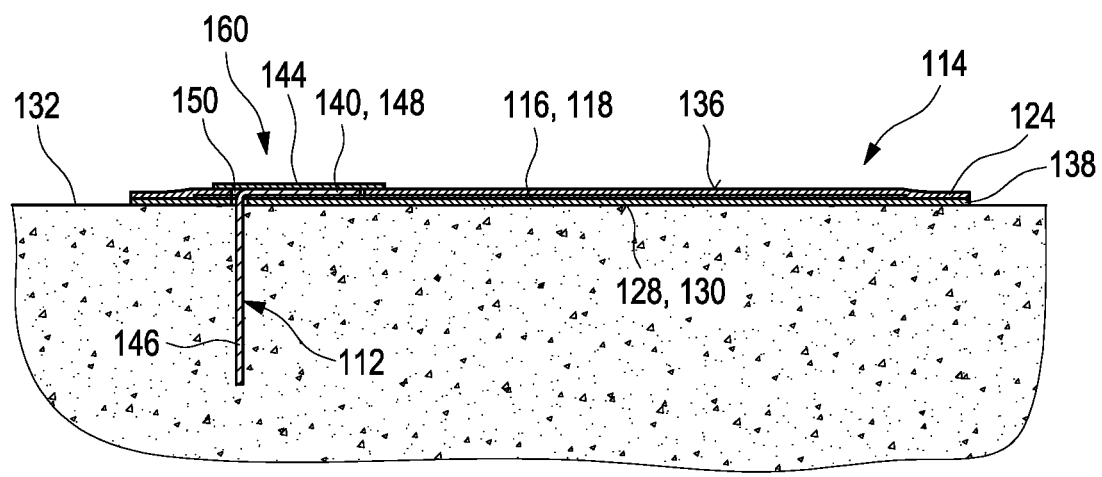
Figure 3:
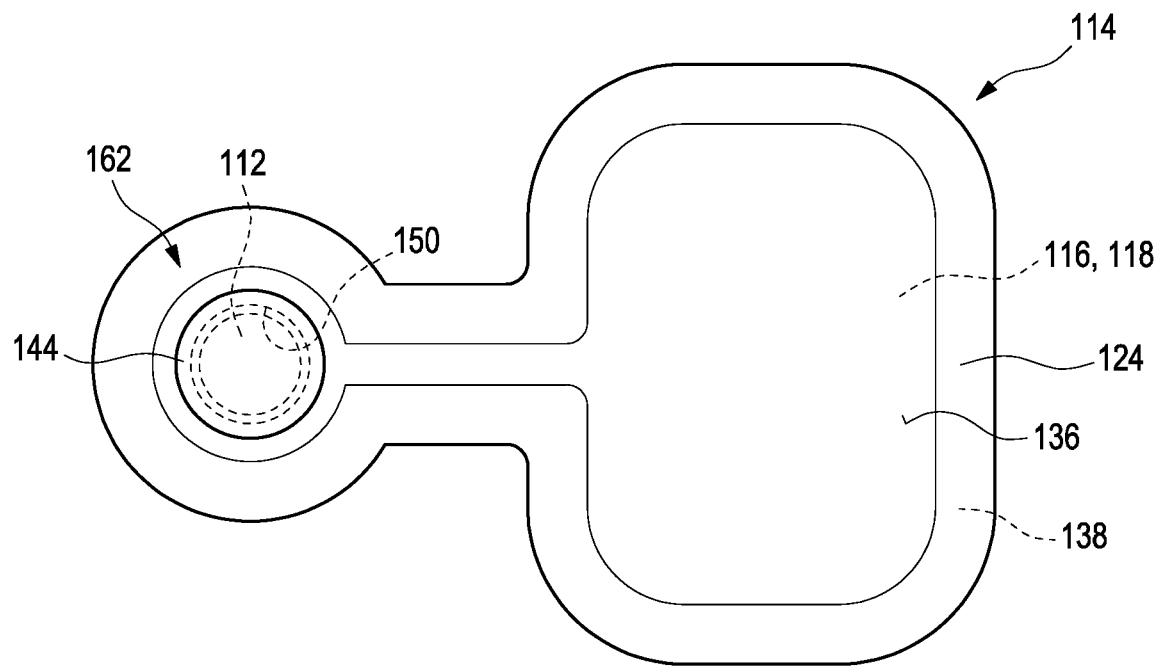
Figure 3:
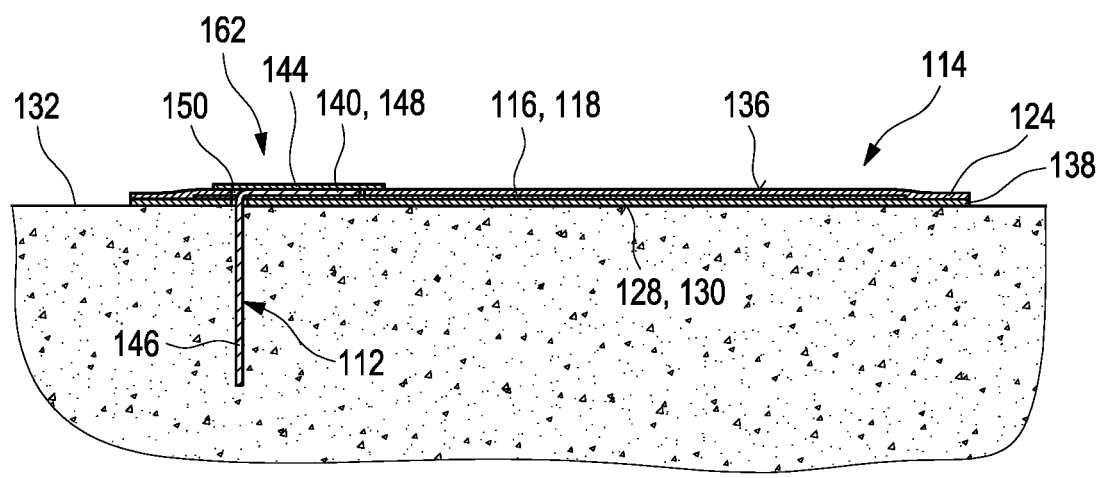
Figure 4:
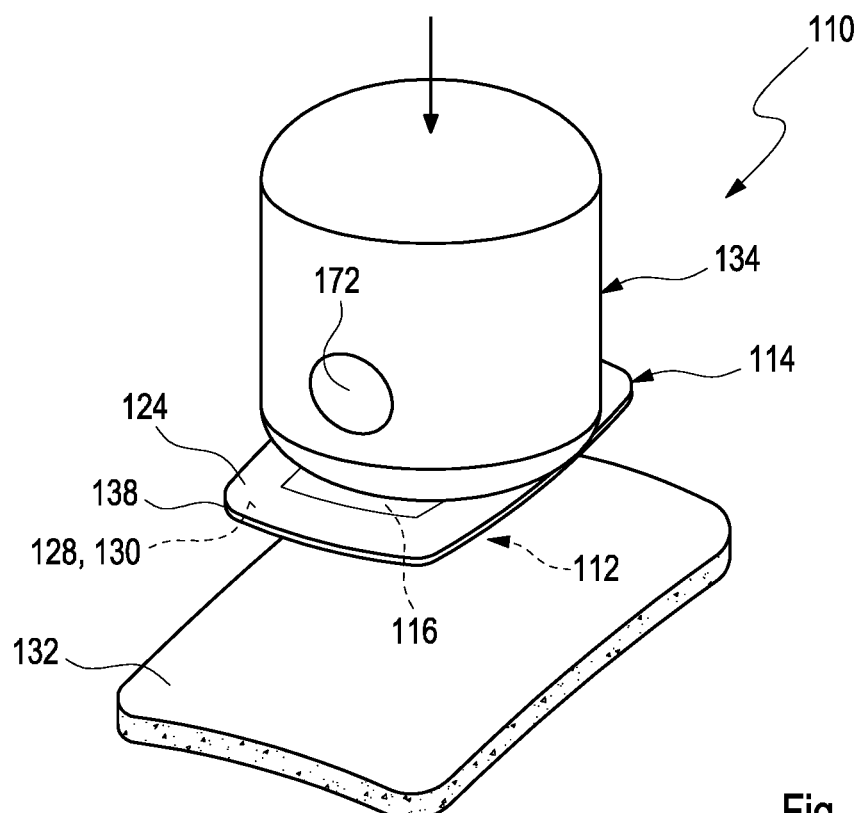
Figure 4:
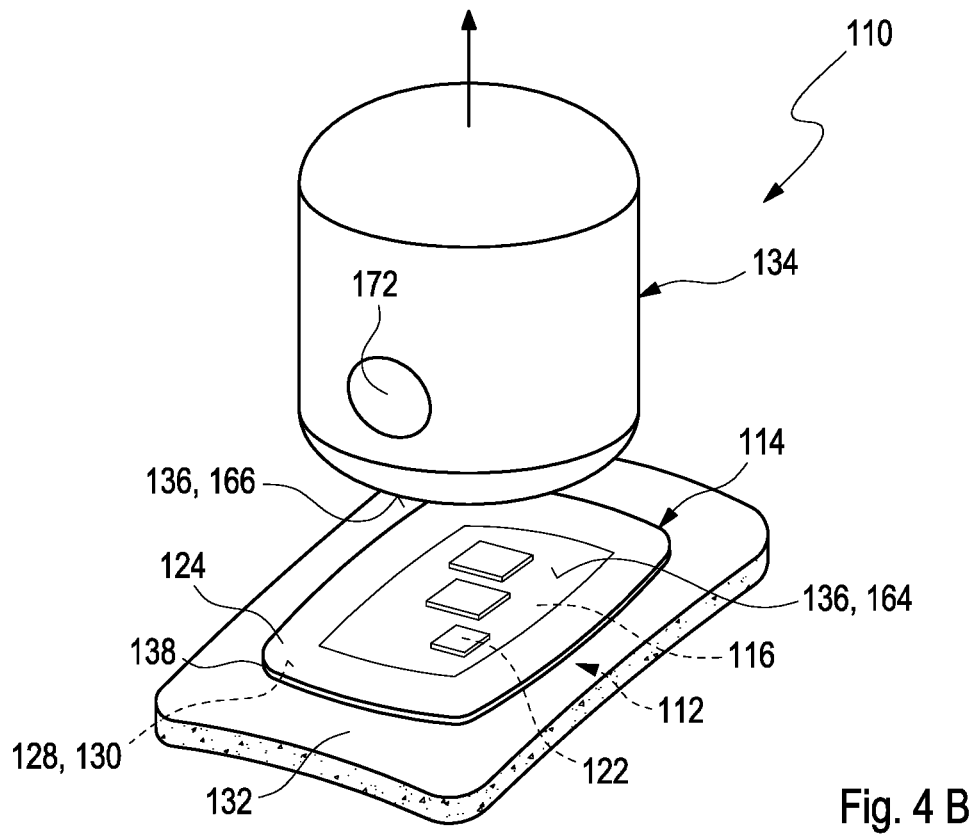
Figure 5:
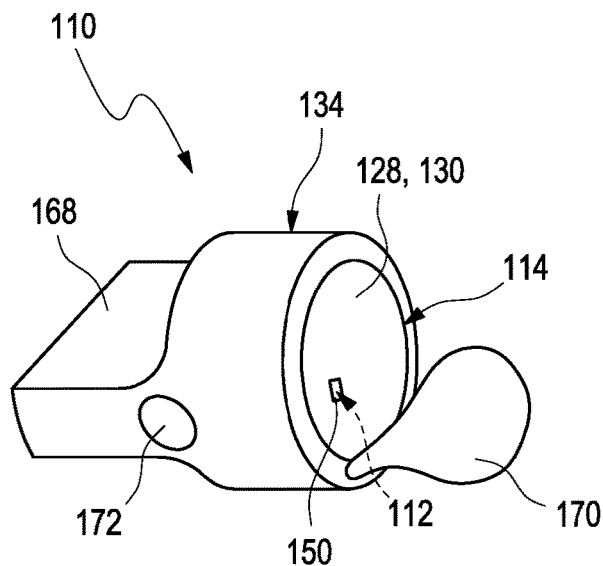
Figure 5:
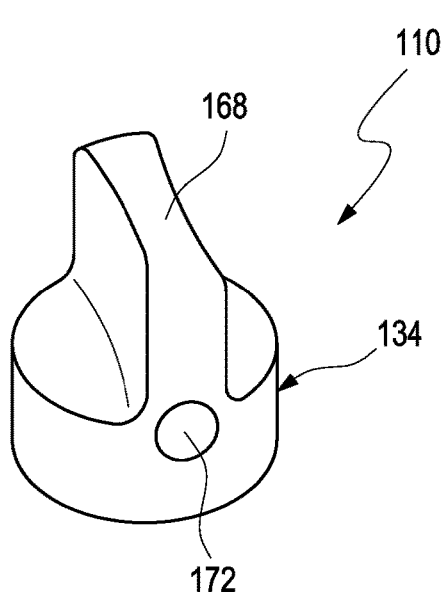

FIGS. 2A to 3B show two embodiments of an analyte sensor 110 and a flexible electronics patch 114 in a top view (FIGS. 2A and 3A) and a cross-sectional view (FIGS. 2B and 3B) illustrating a versatile positioning of the analyte sensor 112 and the corresponding opening 150. The analyte sensor 112 and the corresponding opening 150 may be located centrally within the flexible electronics patch 114, as shown in FIG. 1. However, as shown in FIGS. 2A and 2B, the analyte sensor 112 and the corresponding opening 150 may also be located in an off-centered position 160 within the flexible electronics patch 114, or, as shown in FIGS. 3A and 3B, the analyte sensor 112 and the corresponding opening 150 may also be located in a peripheral position 162 within the flexible electronics patch 114.

The sensor system 110 comprises at least one applicator unit 134 for applying the flexible electronics patch 114 to the skin 132 of the user. FIGS. 4A and 4B illustrate the process of applying the sensor system 110, in particular the flexible electronic patch 114, to the skin 132 of the user. The sensor system 110, in particular the flexible electronics patch 114, comprises at least one first adhesive layer 128 on a lower side 130 of the flexible electronics patch 114, configured for adhering the flexible electronics patch 114 to the skin 132 of the user. The sensor system 110 further comprises at least one second adhesive layer 136 for adhering the flexible electronics patch 114 to the applicator unit 134 before applying the flexible electronics patch 114 to the skin 132 of the user. An adhesive force of the second adhesive layer 136 may be lower than an adhesive force of the first adhesive layer 128 such that when the flexible electronics patch 114 is pressed onto the skin 132 by the applicator unit 134 and the applicator unit 134 is removed as depicted in FIG. 4B, the flexible electronics patch 114 is separated from the applicator unit 130 and adheres to the skin 132. In order to achieve the process just described the second adhesive layer 136 may be part of one or both of the applicator unit 134 and the flexible electronics patch 114, in particular the flexible protective layer 124, as depicted in FIG. 4B. In particular, the second adhesive layer 136 may be located on at least one of an upper surface 164 of the flexible electronics patch 114 and/or on a lower surface 166 of the applicator unit 134. Specifically, the flexible protective layer 124 may comprise one or both of a plaster 190 or an adhesive strip. Alternatively, the second adhesive layer 136 may also be provided as a separate adhesive layer.

The applicator unit 134 may, in particular, comprise or be implemented as at least one of a grip 168 or a handle, as shown, for example, in FIGS. 5A and 5B and in FIGS. 10A to 10C, that may facilitate the handling of the sensor system 110, in particular, the application of the flexible electronics patch 114 to the skin 132 of the user. The flexible electronics patch 114 comprises at least one first adhesive layer 128 on a lower side 130 of the flexible electronics patch 114. In order to expose the first adhesive layer 128 and adhere the flexible electronics patch 114 to the skin 132 of the user protective sheet 170 may have to be removed, as shown in FIG. 5A. In particular, the lower surface 166 of the applicator unit 134 may exceed the upper surface 164 of the flexible electronics patch 114, as depicted in FIG. 5A, in order to ensure safe transfer and attachment of the flexible electronics patch 114 to the skin 132 of the user.

The applicator unit 134 may, in addition, be configured for inserting the analyte sensor 112 into the body tissue, for example, by at least one driving mechanism that may be triggered by at least one activation button 172 that may be integrated into the applicator unit 134, as illustrated in FIGS. 4A to 5B. Thus, the driving mechanism may be part of the applicator unit 134.

FIG. 6 shows a cross-sectional view of a further embodiment of the sensor system 110 with particular attention paid to the first adhesive layer 128 and the second adhesive layer 136 of the sensor system 110. The adhesive force of the second adhesive layer 136 may be lower than the adhesive force of the first adhesive layer 128 in order to allow the transfer of the flexible electronics patch 114 from the applicator unit 134 onto the skin 132. The adhesive force of the first adhesive layer 128 and the adhesive force of the second adhesive layer 136 may be adjusted in several ways, such as but not limited to the choice of adhesive, a thickness of the adhesive layers, an amount of adhesive used and a size of the adhesive layer. In particular, the size of the adhesive layer may be reduced to an adhesive dot 174, as shown in FIG. 6 for the first adhesive layer 128, or to several adhesive dots 174, as shown in FIG. 6 for the second adhesive layer 136.

FIG. 7 shows a cross-sectional view of a further embodiment of the sensor system 110, in which the analyte sensor 112 may be electrically disconnected from the flexible circuit board 116 before insertion, and the driving mechanism may be configured for electrically contacting the at least one electrical contact 140 of the analyte sensor 112 with the at least one contact pad 142 of the flexible circuit board 116 during insertion. As described above, the driving mechanism may be part of the applicator unit 134. The driving mechanism may for example, comprise a spring 176, as depicted in FIG. 7. The applicator unit 134 may further comprise an insertion needle 178 for inserting the analyte sensor 112 into the body tissue, as also shown in FIG. 7. In particular, the insertion needle 178 may comprise at least one cannula 180, specifically a slotted cannula, having a tip 182 and a lumen 184 for receiving the analyte sensor 112. Before insertion of the analyte sensor 112 into the body tissue, the analyte sensor 112 may be attached to the applicator unit 134 and/or the protective foil 144 by at least one third adhesive layer 186, as depicted in FIG. 7. Additionally or alternatively the analyte sensor 112 may, however, before insertion into the body tissue also be attached to the applicator unit 134 by the at least one third adhesive layer 186 (not shown in the Figures). Thus, the third adhesive layer 186 may be located on one or several of the applicator unit 134, the analyte sensor 112 and the protective foil 144. Just as described for the first adhesive layer 128 and the second adhesive layer 136, the third adhesive layer 186 may be implemented as one or several adhesive dots 174. The analyte sensor 112 may further comprise at least one fourth adhesive layer 188 for attachment of the analyte sensor 112 to the flexible circuit board 116 during insertion. The fourth adhesive layer 188 may, in particular, comprise one or several adhesive dots 174. The fourth adhesive layer 188 may be located on one or both of the analyte sensor 112 and the flexible circuit board 116. The fourth adhesive layer 188 may have a higher adhesive force than the first adhesive layer 186, such that when the analyte sensor 112 is attached to the flexible circuit board 116 and the applicator unit 134 is removed, the analyte sensor 112 remains attached to the flexible circuit board 116. Thus, upon triggering the driving mechanism, the spring 176 may press the insertion needle 178 and the analyte sensor 112 towards the body tissue, as indicated by the arrows in FIG. 7, thus inserting the analyte sensor 112 into the body tissue and transferring the analyte sensor 112 onto the flexible circuit board 116. During the process of insertion the analyte sensor 112 may become electrically connected to the flexible circuit board 116. In particular, the electrical contact 140 of the analyte sensor 112 may be attached to the contact pad 142 of the flexible circuit board 116 during the process of insertion of the analyte sensor 112.

Before the process of insertion is started, a liner 189 that may be at least partially covering the analyte sensor 112 and/or the protective foil 144, as shown in FIG. 7, may have to be removed in order to at least partially expose the fourth adhesive layer 188 and/or the adhesive 145 of the protective foil 144. Upon transfer of the analyte sensor 112 onto the flexible electronics patch 114 the electrically contacting of the at least one electrical contact 140 of the analyte sensor 112 to the at least one contact pad 142 of the flexible circuit board 116 may be implemented or facilitated by an electrically conductive adhesive 191. In particular, the fourth adhesive layer 188 may be or may comprise the electrically conductive adhesive 191. Further, a contact region 193 in which the at least one electrical contact 140 of the analyte sensor 112 may be attached to the contact pad 142 of the flexible circuit board 116 may be sealed, for example in order to protect the electrical contact 140 and/or the contact pad 142 against moisture. Sealing may be implemented by at least one of the adhesive layers, adhesives and adhesive elements of the sensor system 110. Thus, as an example, the adhesive 145 of the protective foil 144 and the fourth adhesive layer 188 may contribute to sealing the contact region 193, for instance by forming a circumferential adhesive area surrounding the contact region 193.

In the embodiment of the sensor system 110 depicted in FIG. 7, the flexible protective layer 124 is implemented as a plaster. Thus, in this particular embodiment, the flexible protective layer 124 comprises at least one adhesive portion 192.

The analyte sensor 112 may be electrically disconnected from the flexible circuit board 116 before insertion, as illustrated in FIG. 7. The sensor system 110 may, however, also be configured in such a way that the analyte sensor may be permanently electrically connected to the flexible circuit board 116 before, during and after insertion. Thus, as illustrated in FIG. 8, the analyte sensor 112 may be electrically connected to the flexible circuit board 116 in a wirebound fashion 194. Insertion may take place under a insertion angle α of less than 90°, for instance at the insertion angle of about 45°, as depicted in FIG. 8. However, insertion may also take place at the insertion angle α of about 90°, as illustrated, for instance, in FIG. 9.

FIG. 9 shows a further embodiment of the sensor system 110, with a sterile assembly 196 comprising at least the following components at least partially: the analyte sensor 112, the flexible analyte sensor shaft 146, the insertion needle 178, the cannula 180. The embodiment shown in FIG. 9, may comprise an applicator unit 134 having a first part 198 and a second part. Further, the applicator unit 134 may not comprise a driving mechanism integrated into the applicator unit 134 for inserting the analyte sensor 112 into the body tissue. Instead, the applicator unit 134 may be at least partially removed by the user. In particular, the first part 198 of the applicator unit 134 may be removed by the user thus exposing at least partially the sterile assembly 196 for manual insertion of the entire sterile assembly 196 or parts of the sterile assembly into the body tissue, as indicated by the arrows in FIG. 9. The second part 200 of the applicator unit 134 may subsequently also be removed to retract and dispose of certain parts of the sterile assembly 196, such as but not limited to the insertion needle 178 and the cannula 180.

FIGS. 10A to 10C illustrate in three steps the process of applying the sensor system 110, in particular, the process of at least partially implementing the analyte sensor 112 into the body tissue of the user. In a first step, illustrated in FIG. 10A, the first part 198 of the applicator unit 134 may be removed, as indicated by the arrows in FIG. 10A. The sterile assembly 196 may remain in the second part 200 of the applicator unit 134. In a second step, illustrated in FIG. 10B the sterile assembly 196 may be at least partially inserted into the body tissue by the driving mechanism. The driving mechanism may be integrated into the applicator unit 134, in particular in the second part 200 of the applicator unit 134. The driving mechanism may be activated by the activation button 172. In a third step, illustrated in FIG. 10C, the second part 200 of the applicator unit 134 may be removed, thus retracting certain parts of the sterile assembly 196, such as but not limited to the insertion needle 178 and the cannula 180, while the analyte sensor 112 may remain at least partially implanted in the body tissue. The retracted second part 200 of the applicator unit 134 may receive the retracted part of the sterile assembly 196 and thus serve as safe needle waste.

FIG. 11 shows a further embodiment of the sensor system 110. In this particular embodiment, the sterile assembly 196 may be at least partially received in a sterile cap 202. The sterile cap 202 may be removed before the at least partial implementation of the analyte sensor 112 into the body tissue to at least partially expose certain parts of the sterile assembly 196, such as but not limited to the analyte sensor 112, the flexible analyte sensor shaft 146, the insertion needle 178 and the cannula 180. The analyte sensor 112, as shown in this embodiment of the sensor system 110, may be inserted manually.

FIG. 12 shows a top view of a further embodiment of the analyte sensor 112 and the flexible electronics patch 114 with particular attention paid to a sealing ring 204 surrounding the at least one contact region 193 in which the at least one electrical contact 140 of the analyte sensor 112 may be attached to the contact pad 142 of the flexible circuit board 116. Thus, the sealing of the contact region 193 may be achieved by different means such as but not limited to the adhesive layers, the adhesives and adhesive elements as illustrated in FIG. 7. Additionally or alternatively, the sealing ring 204 may contribute to the sealing of the contact region 193, as illustrated in FIG. 12.

Figure 13:
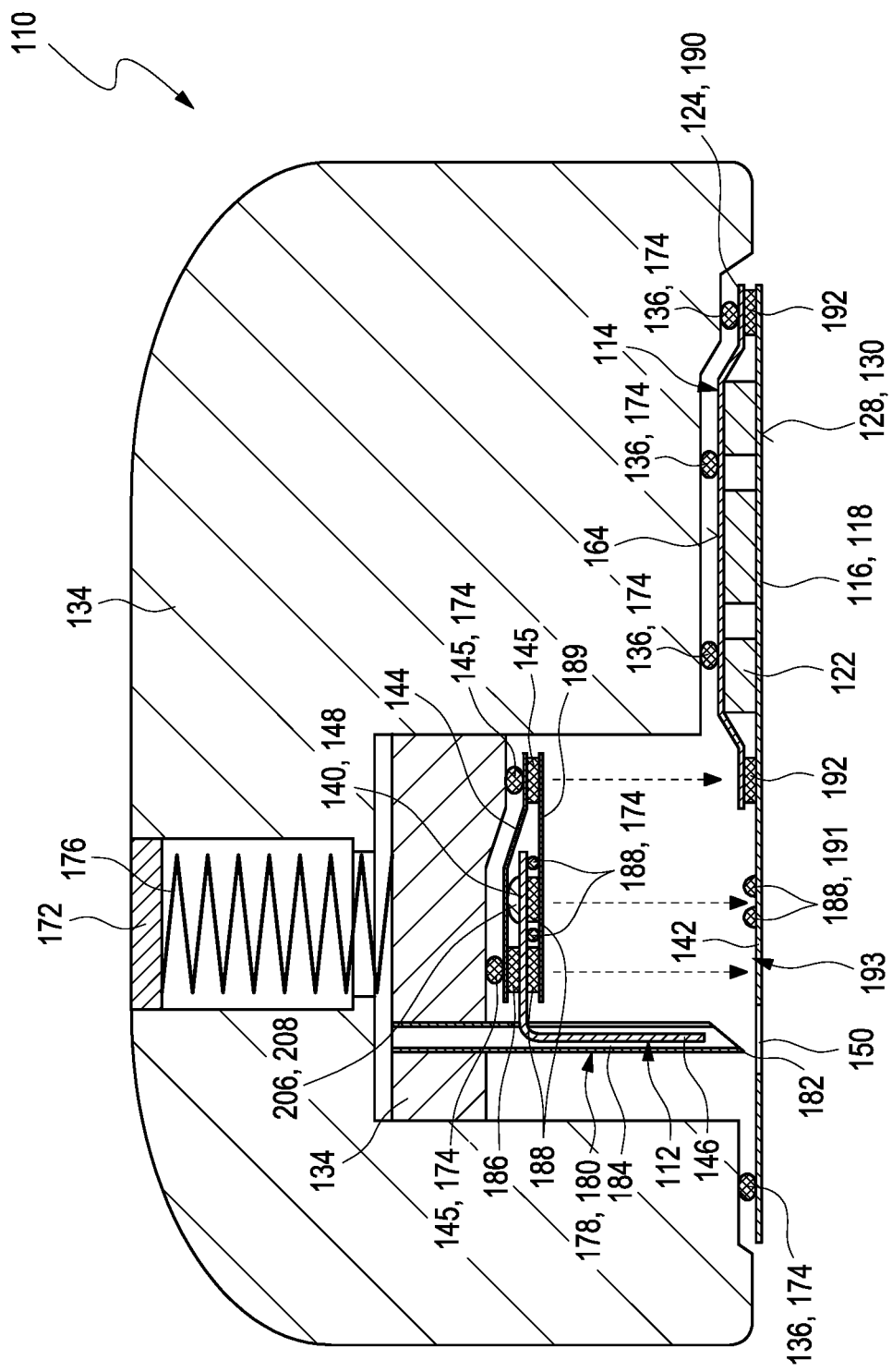
Figure 14:
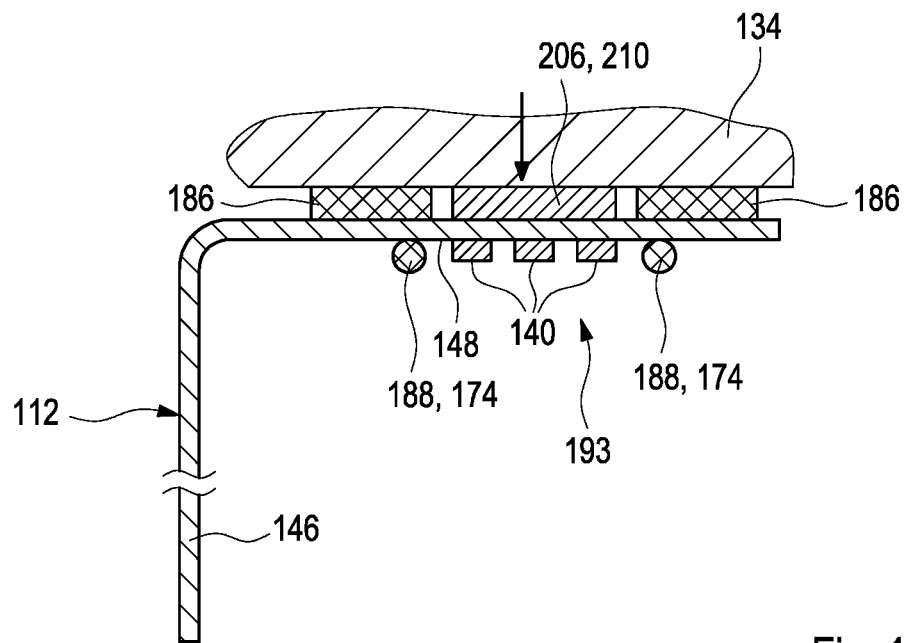
Figure 14:
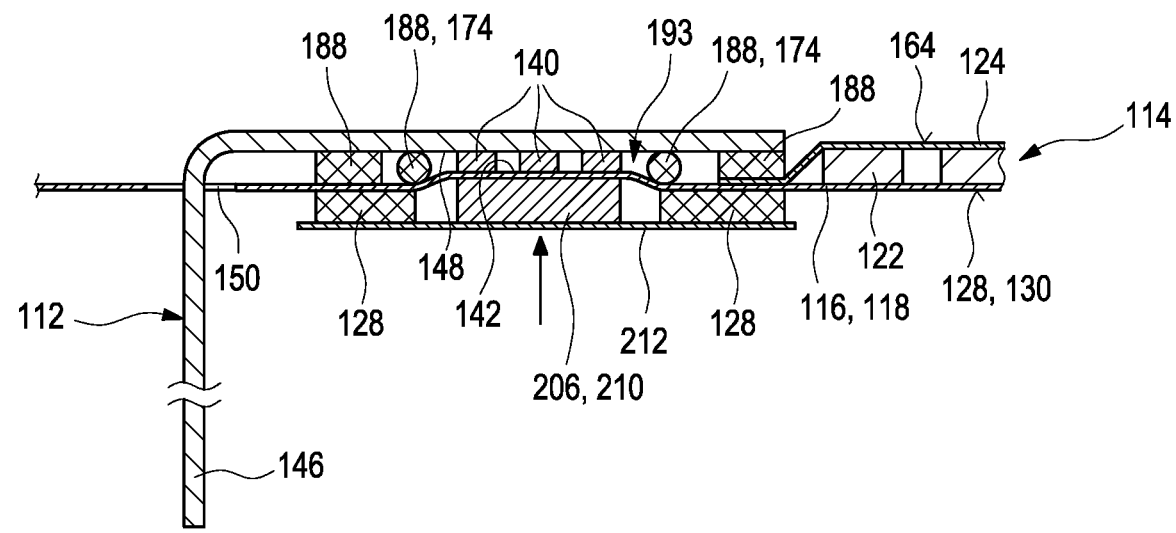
Figure 15:
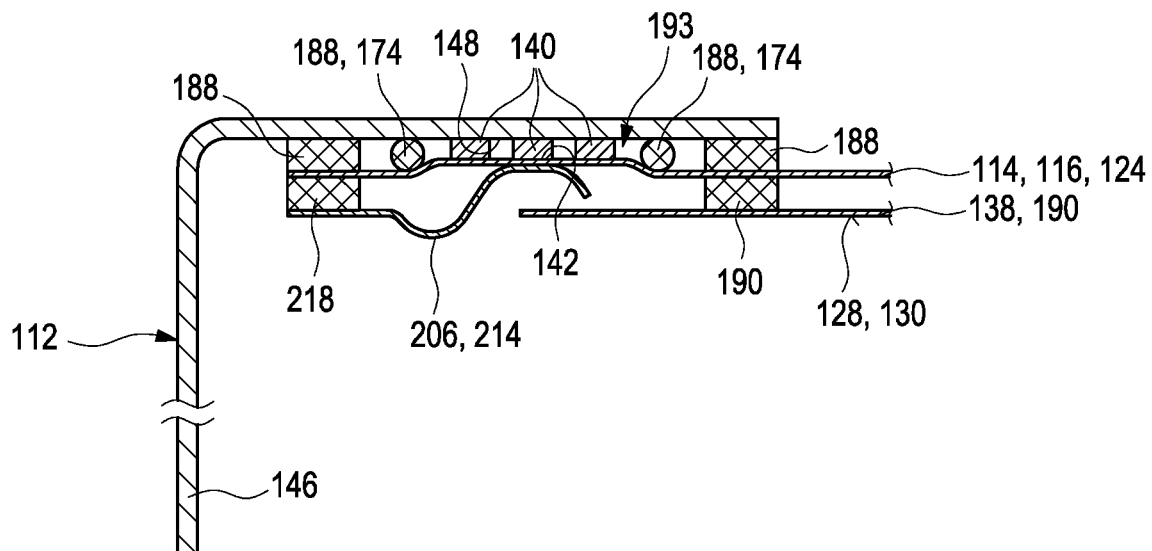
Figure 15:
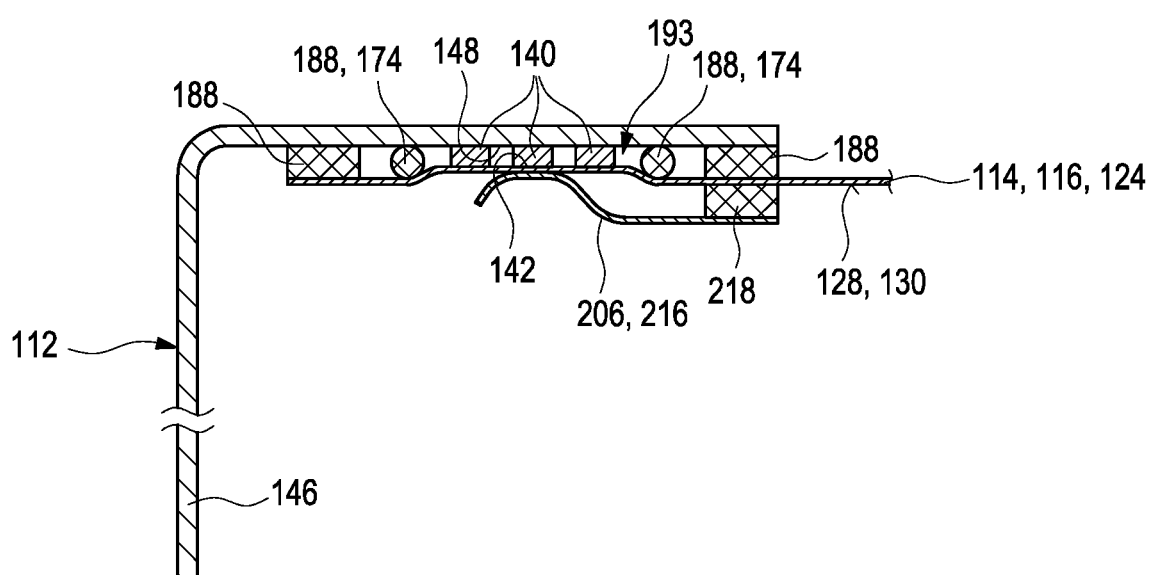

As described above, and illustrated, for example, in FIGS. 7 and 13, the analyte sensor 112 may be electrically disconnected from the flexible circuit board 116 before insertion. In such an embodiment, the sensor system 110 may further comprise a pressing element 206 for pressing the electrical contact 140 of the analyte sensor 112 onto the contact pad 142 of the flexible circuit board 116 once the analyte sensor 112 has been transferred onto the flexible electronic patch 114. Additionally or alternatively, the pressing element 206 may press on the sealing ring 204 or on one or several of the adhesive layers that may contribute to sealing the contact region 193, for instance by forming a circumferential adhesive area surrounding the contact region 193. Thus, the pressing element 206 may contribute to establishing or maintaining an electrical connection between the analyte sensor 112 and the flexible circuit board 116 and/or the pressing element 206 may contribute to sealing the contact region 193. The pressing element 206 may be implemented as a thickening 208, as shown in FIG. 13.

The pressing element 206 may in particular be an adhesive pressing element 210 that may comprise an adhesive that may expand, specifically when in contact with oxygen, such as but not limited to a hydrocolloid. Thus, removal of the liner 189 may expose the adhesive pressing element 210 to oxygen in such a way that the adhesive pressing element 210 may start expanding during or after insertion of the analyte sensor 112 into the body tissue and may keep expanding for a limited time after insertion of the analyte sensor 112 into the body tissue. The expansion process may ensure that the adhesive pressure element 210 may press against the electrical contact pad 142 of the flexible circuit board 116, as shown in FIG. 14B and illustrated by the arrow. Additionally or alternatively, the adhesive pressure element 210 may press against the electrical contact 140 and the contact portion of the analyte sensor 112, as shown in FIG. 14A and illustrated by the arrow. The adhesive pressing element 210 may specifically be attached to the analyte sensor 112 as shown in FIG. 14A. Additionally or alternatively, the adhesive pressing element 210 may be attached to the applicator unit 134 or the protective foil 144. Further, the adhesive pressing element 210 may be attached to a further layer 212 of the sensor system 110 that may be attached to the flexible electronics board 114, for example by the first adhesive layer 128, as illustrated in FIG. 14B. Additionally or alternatively, the adhesive pressing element 210 may be attached to the flexible electronics patch 114, in particular to the lower side 130 of the flexible electronics patch. A particular advantage of the embodiments shown in FIGS. 14A and 14B is that the adhesive pressing element allows a particularly slim design of the sensor system 110.

FIGS. 15A and 15B show two further embodiments of the sensor system 110 in a partial view, both embodiments comprising a variation of the pressing element 206. In the case of FIG. 15A the pressing element 206 is implemented as a doubly-bent metal sheet 214 that may be pushed over or folded over the contact region 193 in such a way as to exert pressure on the contact pad 142, as shown in FIG. 15A, thus establishing or maintaining the electrical connection between the electrical contacts 140 of the analyte sensor 112 and the contact pad 142 of the flexible circuit board 116. In a further embodiment shown in FIG. 15B, the pressing element 206 may be implemented as a shape-memory alloy sheet 216. Again, the shape-memory alloy sheet 216 may be pushed over or folded over the contact region 193 in such a way as to exert pressure on the contact pad 142, thus establishing or maintaining the electrical connection between the electrical contacts 140 of the analyte sensor 112 and the contact pad 142 of the flexible circuit board 116. In particular, the shape-memory alloy sheet 216 may have a shape of a pressure spring, as shown in FIG. 15B, in a hot state and may keep this shape upon cooling. Specifically, the shape-memory alloy sheet may have a heat-activatable shape memory that may, in particular, be activatable by the body heat of the user or by heat generated by an appropriate voltage pulse or an appropriated current pulse. The pressing element 206, in particular the doubly-bent metal sheet or the shape-memory alloy sheet, may be attached to the flexible electronics patch 112 by a pressing element adhesive 218, as shown in FIGS. 15A and 15B.

LIST OF REFERENCE NUMBERS 110 sensor system
112 analyte sensor
114 flexible electronics patch
116 flexible circuit board
118 flexible substrate
120 conductive path
122 electronics component
124 flexible protective layer
126 upper side of the flexible circuit board
128 first adhesive layer
130 lower side of the flexible electronics patch
132 skin
134 applicator unit
136 second adhesive layer
138 flexible bottom layer
140 electrical contact
142 contact pad
144 protective foil
145 adhesive of the protective foil
146 flexible analyte sensor shaft
147 working electrode
148 contact portion
149 further electrode
150 opening
152 insertion needle
154 printed electronics component
156 printed conductive lead
158 flexible foil
159 application-specific integrated circuit
160 off-centered position
162 peripheral position
164 upper surface of the flexible electronics patch
166 lower surface of the applicator unit
168 grip
170 protective sheet
172 activation button
174 adhesive dot
176 spring
178 insertion needle
180 cannula
182 tip
184 lumen
186 third adhesive layer
188 fourth adhesive layer
189 liner
190 plaster
191 electrically conductive adhesive
192 adhesive portion of plaster
193 contact region
194 wire-bound electrical connection
196 sterile assembly
198 first part of applicator unit
200 second part of the applicator unit
202 sterile cap
204 sealing ring
206 pressing element
208 thickening
210 adhesive pressing element
212 further layer
214 doubly-bent metal sheet
216 shape-memory alloy sheet
218 pressing element adhesive

The invention claimed is:

1. A sensor system, comprising
at least one analyte sensor configured for at least partial implementation into a body tissue of a user, each of the at least one analyte sensor including at least one electrical contact;
at least one flexible electronics patch, the flexible electronics patch comprising
at least one flexible circuit board having a flexible substrate and a plurality of conductive paths on the flexible substrate, each of the at least one flexible circuit board including at least one contact pad;
at least one electronics component for performing at least one analyte measurement using the at least one analyte sensor, each electronics component being one of attached to or integrated into the flexible circuit board;
at least one flexible protective layer, the protective layer at least partially covering an upper side of the flexible circuit board; and
at least one first adhesive layer on a lower side of the flexible electronics patch, configured for adhering the flexible electronics patch to the skin of the user;
at least one applicator unit for applying the flexible electronics patch to the skin of the user;
wherein the applicator unit comprises at least one insertion needle for inserting the at least one analyte sensor into the body tissue, and
wherein the sensor system, before insertion of the at least one analyte sensor into the body tissue, is configured in a configuration, in which the at least one analyte sensor is electrically disconnected from the flexible circuit board before insertion, and is configured for electrically contacting at least one electrical contact of the at least one analyte sensor with at least one contact pad of the flexible circuit board during insertion.

2. The sensor system according to claim 1 further including at least one second adhesive layer for adhering the flexible electronics patch to the applicator unit before applying the flexible electronics patch to the skin of the user, wherein an adhesive force of the second adhesive layer is lower than an adhesive force of the first adhesive layer, such that when the flexible electronics patch is pressed onto the skin by the applicator unit and the applicator unit is removed, the flexible electronics patch is separated from the applicator unit and adheres to the skin.

3. The sensor system according to claim 2, wherein, before insertion of the at least one analyte sensor into the body tissue, the at least one analyte sensor is attached to the applicator unit by at least one third adhesive layer, wherein the at least one analyte sensor comprises at least one fourth adhesive layer for attachment of the at least one analyte sensor to the flexible circuit board during insertion, wherein the fourth adhesive layer has a higher adhesive force than the third adhesive layer, such that when the at least one analyte sensor is attached to the flexible circuit board and the at least one applicator unit is removed, the at least one analyte sensor remains attached to the flexible circuit board.

4. The sensor system according to claim 1, wherein the sensor system further comprises at least one flexible bottom layer, wherein the flexible circuit board is located in between the flexible bottom layer and the flexible protective layer.

5. The sensor system according to claim 4, wherein the lower side is located on the flexible bottom layer, wherein the first adhesive layer is located on the lower side of the flexible bottom layer, for adhesion of the flexible bottom layer to the skin.

6. The sensor system according to claim 1, wherein the flexible circuit board has a thickness of 10 to 250 µm.

7. The sensor system according to claim 6, wherein the flexible circuit board has a thickness of 50 to 100 µm.

8. The sensor system according to claim 1, wherein the sensor system further comprises at least one protective foil for covering the at least one analyte sensor and the contact pad when the electrical contact of the at least one analyte sensor is attached to the contact pad of the flexible circuit board.

9. The sensor system according to claim 1, wherein one or both of the flexible circuit board or the at least one analyte sensor comprise at least one sealing ring surrounding at least one contact region in which the at least one electrical contact of the at least one analyte sensor is attached to the contact pad of the flexible circuit board.

10. The sensor system according to claim 1, wherein the applicator unit comprises at least one of a grip or handle for pressing the flexible electronics patch onto the skin of the user.

11. The sensor system according to claim 1, wherein the at least one flexible electronics patch comprises at least one antenna for one or both of sending or receiving information.

12. The sensor system according to claim 1 and further including a driving mechanism configured for electrically contacting at least one electrical contact of the at least one analyte sensor with at least one contact pad of the at least one flexible circuit board during insertion.

13. A method of manufacturing a sensor system according to claim 1, the method comprising:
  i. manufacturing at least one flexible electronics patch by:
     a. providing at least one flexible circuit board having a flexible substrate and a plurality of conductive paths on the flexible substrate;
     b. providing at least one electronics component for performing at least one analyte measurement using at least one analyte sensor;
     c. assembling each of the at least one electronics component with the flexible circuit board, by one or both of attaching the electronics component to the flexible circuit board or integrating the electronics component into the flexible circuit board, the electronics component and the flexible circuit board having a first configuration with each of the at least one analyte sensor being electrically disconnected from the flexible circuit board, and a second configuration with each analyte sensor having at least one electrical contact electrically contacting a contact pad of the flexible circuit board;
     d. providing at least one flexible protective layer;
     e. at least partially covering an upper side of the flexible circuit board with the protective layer; and
     f. providing at least one first adhesive layer on a lower side of the flexible electronics patch, configured for adhering the flexible electronics patch to the skin of the user;
  ii. providing at least one applicator unit for applying the flexible electronics patch to the skin of the user;
  iii. providing at least one second adhesive layer; and
  iv. adhering the flexible electronics patch to the applicator unit by using the second adhesive layer.

\* \* \* \* \*